US010686928B2

(12) United States Patent
Nguyen

(10) Patent No.: US 10,686,928 B2
(45) Date of Patent: Jun. 16, 2020

(54) APPARATUS, METHOD, AND SYSTEM OF COGNITIVE COMMUNICATION ASSISTANT FOR ENHANCING ABILITY AND EFFICIENCY OF USERS COMMUNICATING COMPREHENSION

(71) Applicant: FUVI COGNITIVE NETWORK CORP., Framingham, MA (US)

(72) Inventor: Phu-Vinh Nguyen, Sherborn, MA (US)

(73) Assignee: FUVI COGNITIVE NETWORK CORP., Framingham, MA (US)

( * ) Notice: Subject to any disclaimer, the term of this patent is extended or adjusted under 35 U.S.C. 154(b) by 0 days.

(21) Appl. No.: 16/593,260

(22) Filed: Oct. 4, 2019

(65) Prior Publication Data

US 2020/0036829 A1    Jan. 30, 2020

Related U.S. Application Data

(63) Continuation of application No. 16/451,326, filed on Jun. 25, 2019, now Pat. No. 10,477,009, which is a
(Continued)

(51) Int. Cl.
*H04M 1/725* (2006.01)
*H04M 1/02* (2006.01)
(Continued)

(52) U.S. Cl.
CPC ........... *H04M 1/72544* (2013.01); *A61B 5/01* (2013.01); *A61B 5/021* (2013.01); *A61B 5/0476* (2013.01);
(Continued)

(58) Field of Classification Search
CPC .. H04M 1/0216; H04M 3/56; H04M 1/72555; H04N 7/14
See application file for complete search history.

(56) References Cited

U.S. PATENT DOCUMENTS 7,412,261 B2 *  8/2008  Tutikawa ............ H04M 1/0214
                                                      361/679.27
8,887,300 B1   11/2014  Gates et al.
(Continued)

OTHER PUBLICATIONS

Choubeilla Maaoui, et al., "Emotion Recognition through Physiological Signals for Human-Machine Communication", Cutting Edge Robotics, 2010, pp. 317-332.
(Continued)

*Primary Examiner* — Wen W Huang
(74) *Attorney, Agent, or Firm* — Edell, Shapiro & Finnan, LLC

(57) ABSTRACT

A communication apparatus, a method, a computer readable medium, and a system providing communication with cognitive and visual assistance. The cognitive assistance and visual assistance is provided during a communication between a first communication apparatus with at least one second communication apparatus via a network. The first communication apparatus captures communication data comprising visual and audio information obtained from the communication and captures synchronized cognitive and emotional data generated from the user during the communication with the second communication apparatus. The communication data and the synchronized cognitive and emotional data is stored and converted into a visual form comprising at least one of synchronized text, symbols, sketches, images, and animation. The visual form is displayed on a display of the first communication apparatus.

11 Claims, 20 Drawing Sheets

Related U.S. Application Data continuation of application No. 16/213,577, filed on Dec. 7, 2018, now Pat. No. 10,367,931.

(60) Provisional application No. 62/668,939, filed on May 9, 2018.

(51) Int. Cl.

| | | |
|---|---|---|
| *H04M 1/656* | (2006.01) | |
| *A61B 5/16* | (2006.01) | |
| *A61B 5/00* | (2006.01) | |
| *A61B 5/01* | (2006.01) | |
| *A61B 5/021* | (2006.01) | |
| *A61B 5/0476* | (2006.01) | |
| *A61B 5/0205* | (2006.01) | |

(52) U.S. Cl.
CPC ............ *A61B 5/165* (2013.01); *A61B 5/6803* (2013.01); *H04M 1/0216* (2013.01); *H04M 1/656* (2013.01); *A61B 5/02055* (2013.01); *H04M 2250/16* (2013.01); *H04M 2250/74* (2013.01)

(56) References Cited

U.S. PATENT DOCUMENTS

| | | | |
|---|---|---|---|
| 9,711,056 B1* | 7/2017 | Nguyen | A61B 5/7425 |
| 10,015,442 B1* | 7/2018 | Maltezos | G06F 1/1677 |
| 10,218,937 B2 | 2/2019 | Wang | |
| 2003/0118974 A1 | 6/2003 | Obrador | |
| 2005/0223078 A1 | 10/2005 | Sato et al. | |
| 2007/0057866 A1* | 3/2007 | Lee | H04M 1/0218 345/1.1 |
| 2007/0162606 A1 | 7/2007 | Chen et al. | |
| 2007/0273611 A1 | 11/2007 | Torch | |
| 2009/0171901 A1 | 7/2009 | Bathiche et al. | |
| 2010/0064244 A1 | 3/2010 | Kilpatrick, II et al. | |
| 2010/0079573 A1 | 4/2010 | Isaac | |
| 2010/0085414 A1 | 4/2010 | Eun et al. | |
| 2010/0146052 A1 | 6/2010 | Pare et al. | |
| 2012/0275292 A1 | 11/2012 | Micu et al. | |
| 2012/0295589 A1 | 11/2012 | Alexander et al. | |
| 2013/0021266 A1* | 1/2013 | Selim | G06F 3/0487 345/173 |
| 2013/0063256 A1 | 3/2013 | Tartz et al. | |
| 2013/0194374 A1 | 8/2013 | Kieft et al. | |
| 2014/0192134 A1 | 7/2014 | Jung et al. | |
| 2014/0195619 A1 | 7/2014 | Hodjat | |
| 2014/0267543 A1* | 9/2014 | Kerger | H04W 4/21 348/14.02 |
| 2015/0116126 A1 | 4/2015 | Hyde et al. | |
| 2015/0207970 A1 | 7/2015 | Min et al. | |
| 2016/0042648 A1 | 2/2016 | Kothuri | |
| 2016/0065724 A1* | 3/2016 | Lee | H04M 1/72569 455/556.1 |
| 2017/0118318 A1* | 4/2017 | Ma | H04M 1/0235 |
| 2017/0171441 A1 | 6/2017 | Kearns et al. | |
| 2017/0310927 A1 | 10/2017 | West et al. | |
| 2018/0331984 A1 | 11/2018 | McCall | |
| 2018/0332205 A1* | 11/2018 | Hawthorne | H04N 5/232 |

OTHER PUBLICATIONS

International Search Report and Written Opinion in counterpart International Application No. PCT/US2019/31517, dated Jul. 24, 2019, 16 pages.

* cited by examiner

APPARATUS, METHOD, AND SYSTEM OF COGNITIVE COMMUNICATION ASSISTANT FOR ENHANCING ABILITY AND EFFICIENCY OF USERS COMMUNICATING COMPREHENSION

CROSS-REFERENCE TO RELATED APPLICATION

This application is a Continuation Application of U.S. patent application Ser. No. 16/451,326 filed Jun. 25, 2019, which is a Continuation Application of U.S. patent application Ser. No. 16/213,577 filed Dec. 7, 2018, which claims priority from U.S. Provisional Application No. 62/668,939 filed May 9, 2018, the contents of which are incorporated herein by reference in their entireties.

BACKGROUND

1. Field

Apparatuses, methods, systems, and computer readable mediums consistent with the present disclosure broadly relate to cognitive technology, and more particularly, to cognitive communication related technology.

2. Description of Related Art

Nowadays, global communication is more prevalent with technological advances. Communication using electronic devices is widespread. Users use their electronic devices to communicate their daily activities and to interact with friends via social media, online chatting, messaging and multi-media messaging, video and telephone calling, and even playing video games or watching media together using their respective electronic devices.

To accommodate various functionalities required by the users, the electronic devices are also advancing, for example, by having faster processing, more storage capabilities, improved communication mechanisms, and improved user interfaces.

However, there are still many unresolved problems in the art of communication technologies. For example, technologies to allow a user to not only communicate via audio and video but also share his or her actual cognitive state with other users are still needed.

Additionally, there is still a need to develop technologies that could capture data of a conversation of a user and display as much as possible of this data to him or herself to help the user manage his or her working memory performance during the conversation, to further enhance the coherence of the conversation. There is also a need to measure and display actual emotional states of a user together with the above data of the conversation to himself or herself and to his or her friend to enrich the mutual understanding of the information exchanged.

There is yet another need to display the topic of the conversation such as photos, presentation, on a device of the user such as a mobile phone to enrich the content of information exchange and to improve the comprehension of the user during and/or after the conversation. There is yet another need in the art of reviewing, adding notes and comments onto the recorded video conversation, and then save the added notes and/or exchange them with peers. Additionally, the electronic devices that can accommodate cognitive assistance during audio and/or visual communication while being convenient to use (such as small sized and portable) are need.

In other words, there are many areas in the communication provided by various electronic devices that needs further developments and improvements.

The above information is presented as background to help set the stage of the present disclosure. No acquiescence and no determination has been made whether any of the above provided information may be applicable as prior art with regard to the present disclosure.

SUMMARY

Illustrative, non-limiting embodiments may overcome the above disadvantages and other disadvantages not described above, and also may have been developed to provide solutions to other disadvantages and problems that were not described above. However, a method, an apparatus, a system, and a computer readable medium that operates according to the teachings of the present disclosure are not necessarily required to overcome any of the particular problems or disadvantages described above. It is understood that one or more exemplary embodiment is not required to overcome the disadvantages described above, and may not overcome any of the problems described above. The appended claims should be consulted to ascertain the true scope of the present disclosure.

An aspect of the present disclosure is to provide a cognitive communication apparatus.

Another aspect of the present disclosure is to provide a communication method in which cognitive assistance is provided.

Yet another aspect of the present disclosure is to provide a system and a computer readable medium which provide cognitive assistance during communication between one or more users.

According to one or more aspects of the present disclosure, a communication apparatus with cognitive and visual assistance is provided. The communication apparatus includes at least one communication interface configured to connect to at least one network to execute communication with at least one other communication apparatus, at least one communication data capturer configured to capture communication data comprising visual and audio information obtained from the communication and further configured to capture synchronized cognitive and emotional data generated from at least one user during the communication with the at least one other communication apparatus, a memory configured to store the communication data and the synchronized cognitive and emotional data. The communication apparatus further includes at least one communication data converter configured to convert the communication data and the synchronized cognitive and emotional data into a visual form comprising at least one of synchronized text, symbols, sketches, images, and animation and at least one display configured to display the visual form of the communication data and the synchronized cognitive and emotional data converted by the communication data converter.

According to one or more aspects of the present disclosure, a communication method with cognitive and visual assistance is provided. The method includes connecting, by a first communication apparatus, to at least one network to execute communication with at least one second communication apparatus, capturing, by the first communication apparatus, communication data comprising visual and audio information obtained from the communication, capturing, by the first communication apparatus, synchronized cognitive and emotional data generated from at least one user during the communication with the at least one second communication apparatus, storing, by the first communication apparatus, the communication data and the synchronized cognitive and emotional data, converting, by the first communication apparatus, the communication data and the synchronized cognitive and emotional data into a visual form comprising at least one of synchronized text, symbols, sketches, images, and animation, and displaying, on a display of the first communication apparatus, the visual form of the converted communication data and the converted synchronized cognitive and emotional data.

According to one or more aspects of the present disclosure, a non-transitory computer readable medium is provided. The medium is configured to store instructions, which when executed by the processor cause the processor to execute the following operations: connecting a first communication apparatus to at least one network to execute communication with at least one second communication apparatus, capturing communication data comprising visual and audio information obtained from the communication, capturing synchronized cognitive and emotional data generated from at least one user during the communication with the at least one second communication apparatus, storing the communication data and the synchronized cognitive and emotional data, converting the communication data and the synchronized cognitive and emotional data into a visual form comprising at least one of synchronized text, symbols, sketches, images, and animation, and displaying, on a display of the first communication apparatus, the visual form of the converted communication data and the converted synchronized cognitive and emotional data.

According to one or more aspects of the present disclosure, a system of performing communication with cognitive and visual assistance is provided. The system includes at least one sensory device, worn on at least one of a head of a user and a body of the user, which captures sensory signals from the user comprising at least one of brain signals, blood pressure, and skin temperature and a first communication apparatus which communicates with a second communication apparatus via a network. The first communication apparatus includes at least one communication interface configured to connect to at least one network to execute communication with at least one other communication apparatus, at least one communication data capturer configured to capture communication data comprising visual and audio information obtained from the communication and further configured to capture synchronized cognitive and emotional data generated from at least one user during the communication with the at least one other communication apparatus, a memory configured to store the communication data and the synchronized cognitive and emotional data, at least one communication data converter configured to convert the communication data and the synchronized cognitive and emotional data into a visual form comprising at least one of synchronized text, symbols, sketches, images, and animation, and at least one display configured to display the visual form of the communication data and the synchronized cognitive and emotional data converted by the communication data converter.

Additional and/or other aspects will be set forth in part in the description which follows and, in part, will be apparent from the description, or may be learned by practice of exemplary embodiments explained below.

BRIEF DESCRIPTION OF THE DRAWINGS

The accompanying drawings, which are incorporated in and constitute a part of this specification exemplify embodiments and, together with the description, serve to explain and illustrate exemplary embodiments thereof. Specifically.

DETAILED DESCRIPTION OF EXEMPLARY EMBODIMENTS

Figure 1:
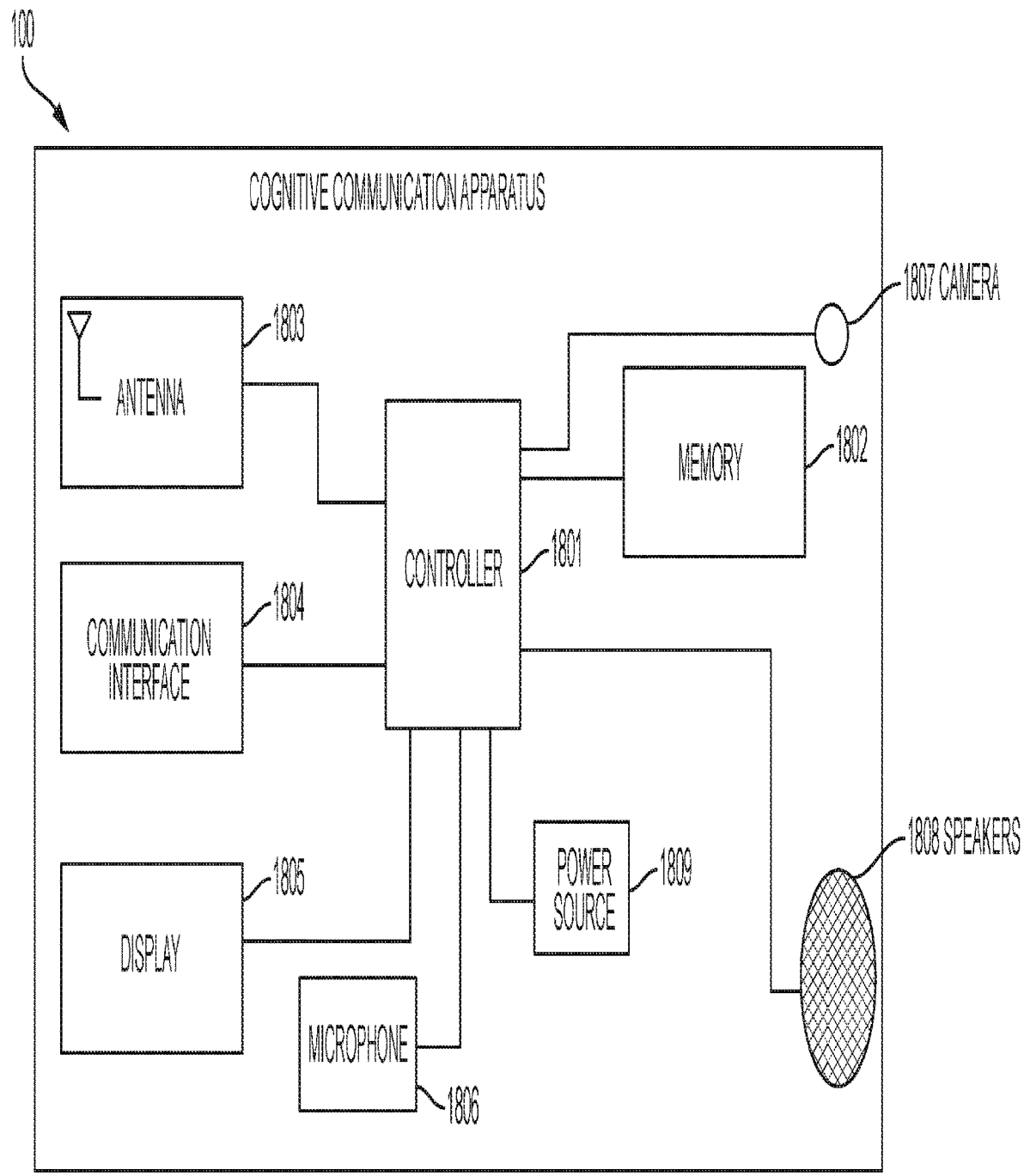
FIG. 1 is a block diagram illustrating a configuration of a cognitive communication apparatus, according to an exemplary embodiment.

Exemplary embodiments will now be described in detail with reference to the accompanying drawings. Exemplary embodiments may be embodied in many different forms and should not be construed as being limited to the illustrative exemplary embodiments set forth herein. Rather, exemplary embodiments are provided so that this disclosure will be thorough and complete, and will fully convey the illustrative concept to those skilled in the art. Also, well-known functions or constructions may be omitted to provide a clear and concise description of exemplary embodiments. The claims and their equivalents should be consulted to ascertain the true scope of an inventive concept. Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary embodiments and techniques illustrated in the drawings and described below.

According to exemplary, non-limiting embodiments, cognitive and/or emotional assistance is provided to a user during and/or after having a conversation with another user or users. According to an exemplary embodiment, a conversation may be a telephonic or a video conference.

According to yet another exemplary, non-limiting embodiment, a portable apparatus provides for cognitive or emotional assistance of contents such as visual and audio information captured during a conversation with another user for example. This visual and audio information may then be synchronized with cognitive or emotional states of the user and may include notes and/or further comments.

According to yet another exemplary, non-limiting embodiment, an apparatus is compact and is portable such as a mobile terminal but yet provides cognitive assistance during and/or after the communication.

For example, U.S. Pat. No. 9,711,056 to Nguyen describes capturing, detecting, and identifying different types of emotional stimulation generated by human organs while the human is exploring and observing the environment, also incorporated herein by reference for its helpful descriptions.

Additionally, U.S. patent application Ser. No. 15/870,210 to Nguyen filed on Jan. 12, 2018, incorporated herein by reference for its helpful descriptions, describes assisting a user in learning, review, and memorization. '210 application describes capturing, displaying, and processing learning data.

However, there is still a need for capturing, displaying, and processing communication data. There is a need to provide cognitive assistance as it relates to communication and communication data.

There is a need to build an apparatus, a method, and a system which is convenient for the user in daily use such that it is portable (easy to carry) and has mobile communication and data communication available so that the user may socialize with other users via social networkings, messaging, and video/audio conversations while also providing cognitive assistance. That is, an electronic device is needed in which the user may continue with his daily functions and use of an electronic device while having additional cognitive assistance, as described in greater detail below in various exemplary embodiments. The provided cognitive assistance may include capturing the conversation and the emotions state of the user, display the captured material during conversation and social networking, build correlations between the conversation and insights.

FIG. 1 is a block diagram illustrating a configuration of a cognitive communication apparatus, according to an exemplary embodiment.

As shown in FIG. 1, the cognitive communication apparatus 100 includes a controller 1801, which controls the overall operations of the apparatus 100 and/or components of the apparatus 100. The controller 1801 may include at least one processor such as a central processing unit and a graphics processor.

The apparatus 100 also includes a memory 1802. The memory 1802 may include random access memory (RAM) and read only memory (ROM). The memory 1802 is an internal memory which stores an operating system (OS) for running the cognitive communication apparatus, one or more applications, system software, and user data. The memory 1802 may include an external memory such as a memory card (SD card, SIM card, microSD card, and so on).

The cognitive communication apparatus further includes an antenna 1803 and a communication interface 1804. The communication interface 1804 is configured to receive communications data from another device via a network. The communication data may be received via a cellular network and/or via a data network. The communication interface 1804 may include a network card to provide an Ethernet connection and a wireless LAN connection.

The communication interface 1804 is further configured to receive cognitive data indicating user's emotional and/or cognitive state from a cognitive state capturing apparatus, explained in further detail below with reference to FIG. 2. The communication interface 1804 may include one or more of a near field communication (NFC) interface, a Bluetooth communication interface, and an infrared communication interface, for communicating with the cognitive state capturing apparatus (FIG. 2), which is in a vicinity of the cognitive communication apparatus 100.

Additionally, the cognitive communication apparatus 100 includes a display 1805, a microphone 1806 for receiving user input audio data, a camera 1807 for capturing visual data such as the user during the communication, speakers 1808 for outputting audio component of the received communication data, and a power source 1809. Additionally, the cognitive communication apparatus 100 may include an HDMI adapter, a power source outlet, a PC port, and a USB port, by way of an example and not by way of a limitation, as is known in the art.

The display 1805 of the cognitive communication apparatus 100 may be a touch display and may include a number of sensors to capture user input. This is provided by way of an example and not by way of a limitation. The cognitive communication apparatus 100 may be connected to a keyboard and/or other user input interfaces via one or more of the USB ports (not shown).

A cognitive communication apparatus 100 may be a personal computer (PC), a notebook computer, a smart telephone, and so on. These are provided by way of an example and not by way of a limitation.

In order for the cognitive communication apparatus 100 to provide cognitive assistance to the user, the user's cognitive state is captured. FIG. 2 is a block diagram illustrating a configuration of a communication system with cognitive assistance, according to an exemplary embodiment.

Figure 2:
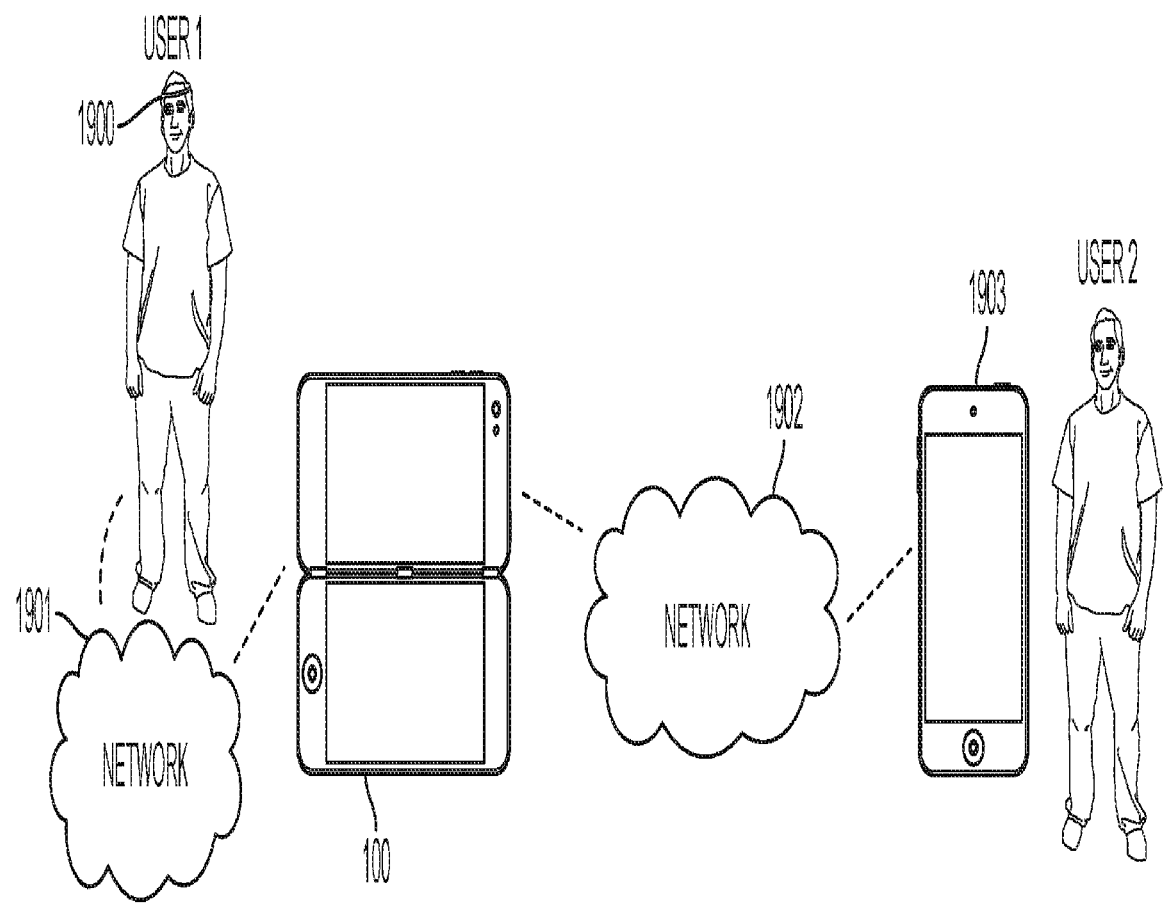
FIG. 2 is a block diagraming illustrating a configuration of a communication system with cognitive assistance, according to an exemplary embodiment.

As shown in FIG. 2, the cognitive communication apparatus 100 communicates with a cognitive state capturing apparatus 1900 via a network 1901 to obtain at least a portion of a cognitive state of the user. The cognitive state capturing apparatus 1900, according to an exemplary embodiment, is described in further detail with reference to FIG. 5A. According to an exemplary embodiment, the cognitive state capturing apparatus 1900 includes a number of sensors to capture cognitive data generated from or by the user and to provide the captured cognitive data to the cognitive communication apparatus 100, as explained in greater detail below. The captured cognitive data may be communicated from the cognitive state capturing apparatus 1900 via a short range communication network such as a Bluetooth network. The cognitive data is analyzed to determine the cognitive state of the user and a level of the cognitive state of the user, as explained in greater detail below.

The cognitive communication apparatus 100 also transmits and receives communication data from another user (user 2) via the user device 1903 using a network 1902. The network 1902 may be a data network, according to an exemplary embodiment. The communication data (visual and audio data) may be recorded by the cognitive state capturing apparatus 1900 or by the cognitive communication apparatus 100.

According to various exemplary embodiments, at least some of the components described to be part of the cognitive communication apparatus 100 may be included in the cognitive state capturing apparatus 1900 and vice versa, as would be readily apparent to one of ordinary skill in the art based on various exemplary embodiments. Additional remote servers may be provided for data analysis, according to an exemplary embodiment, such that the cognitive state capturing apparatus 1900 may be in direct communication with the server or via the cognitive communication apparatus 100.

The cognitive communication apparatus 100 may include only one display where various data is displayed thereon or a plurality of displays. In an exemplary embodiment, explained in further detail below, a dual display apparatus is described but this is provided by way of an example only to help understand exemplary embodiments of the present disclosure and not by way of a limitation.

Figure 3A:
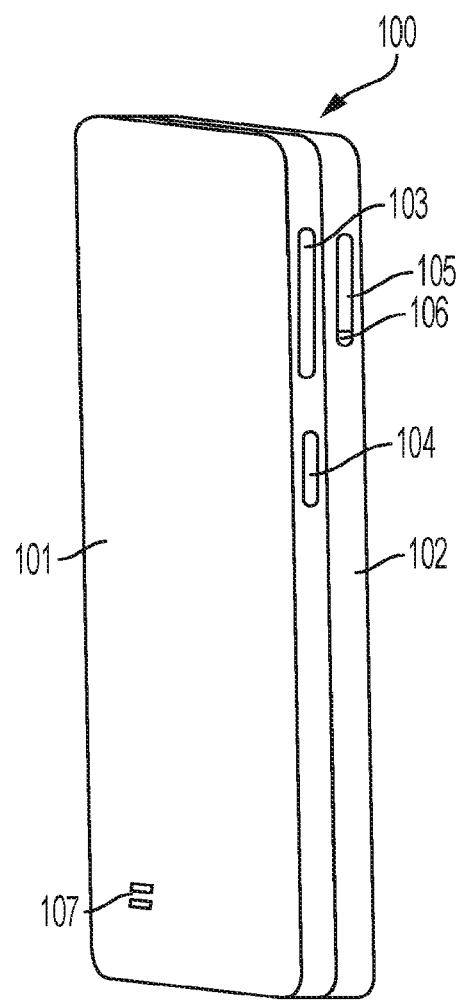
FIG. 3A is a view illustrating an apparatus in a closed state, according to an exemplary embodiment.

FIGS. 3A-3D are views illustrating an apparatus according to one or more exemplary embodiments. The apparatus depicted in the figures is a cognitive or an emotion detection enabled, mobile, portable device such as a dual-display smart phone. FIG. 3A is a view depicting an apparatus 100 in a closed state. The apparatus 100 has two parts: a first part 101 and a second part 102. The first part 101 and the second part 102 have a protective casing on an outer part thereof as depicted in FIG. 3A. No cameras or other components of the apparatus 100 extend to the outside, according to an exemplary embodiment. The first part 101 may have a volume button 103 and a lock state button 104, as would be understood by one of ordinary skill in the art. Additionally, buttons 105 and 106 may be provided on the second part 102 to open the apparatus 100 and to silence the apparatus 100 and a recessed hole 107 may be provided for capturing audio environment. These features are provided by way of an example and are not intended to limit the scope of the present disclosure. According to an exemplary embodiment, since no camera is provided on an outer portion of the parts 101 and 102, sturdiness of the apparatus is improved and complexity of the apparatus is reduced.

The apparatus in its closed state, as depicted in FIG. 3A, is compact to be easily carried by the user. For example, the apparatus in its closed state maybe 4 to 10 inches in length, 2 to 6 inches wide and 0.3-2 inches in depth. These ranges in size are provided by way of an example and not by way of a limitation. Accordingly, the apparatus may be easily carried by a user in a pocket or a purse and is compatible with various device holders, known in the art.

Figure 3B:
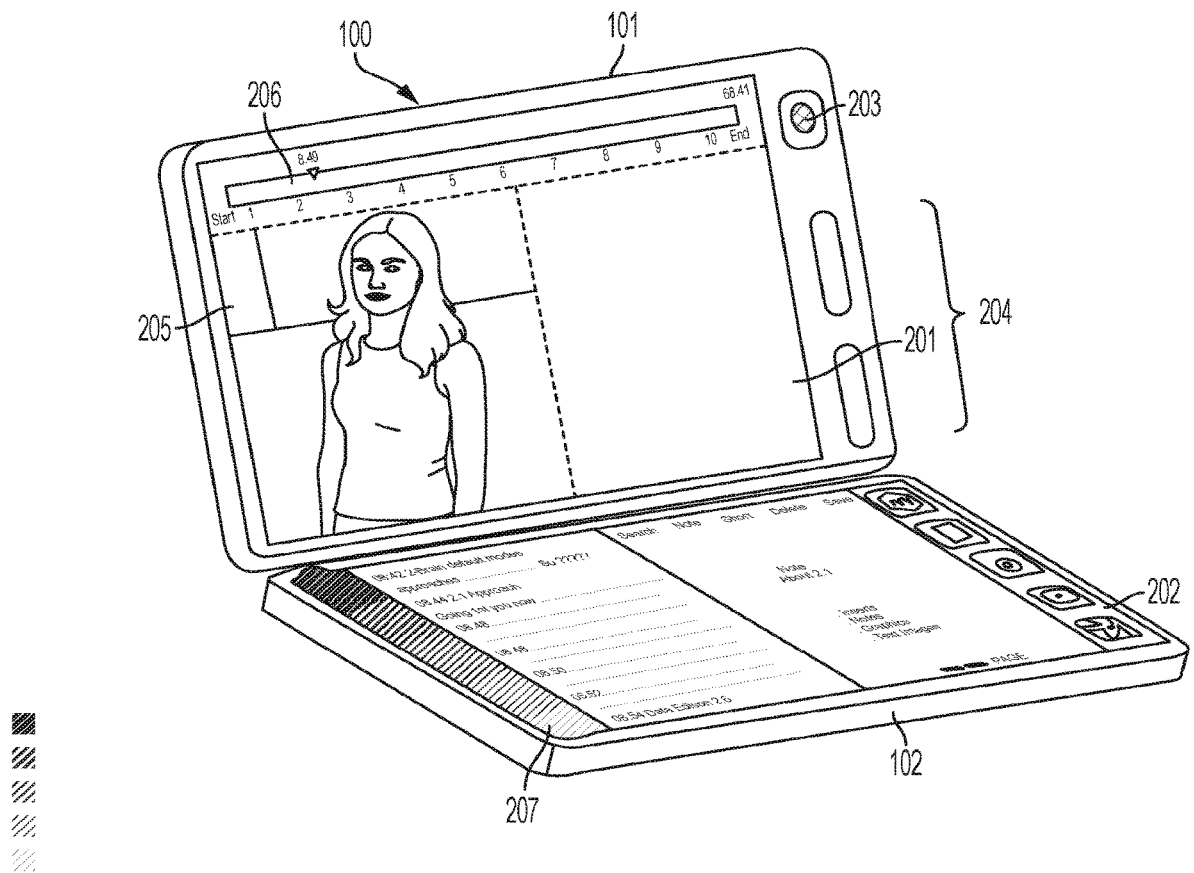
FIG. 3B is a view illustrating an apparatus in a 120-degree open state, according to an exemplary embodiment.

FIG. 3B is a view illustrating an apparatus in a 120 degree open state according to an exemplary embodiment. In FIG. 3B, the apparatus 100 has the first part 101 and the second part 102, each of which includes a display. Specifically, the apparatus 100, according to an example embodiment, has a first display 201 and a second display 202. According to an exemplary embodiment, both displays 201 and 202 may be touch screen displays but this is provided by way of an example and not by way of a limitation. According to other exemplary embodiments, only one of the displays may be a touch screen display or none of the screen displays may be a touch screen display. If none of the displays are a touch screen display, the apparatus may be operated using an add-on keyboard or using keys, joysticks, and other controls as is known in the art.

According to an exemplary embodiment, the display 201 is smaller in size than the display 202. According to yet another exemplary embodiment, the display 202 may be smaller in size than the display 201. One of the displays is made smaller to provide space for a camera 203 and other hardware components 204, according to an exemplary embodiment. The camera 203 allows for selfies and video conferences (video chats) when the apparatus is open 120 degrees. The camera 203 allows the user to capture the environment in a different state, as described in further detail below. The hardware components 204 may include a functional button or a place to return to a home screen in an apparatus, a back button to return to the previous screen, or a display switch button such that contents displayed on the display 201 are switched with contents displayed on the display 202. These explanations are provided by way of an example and not by way of a limitation.

FIG. 3B shows the captured images and/or video and/or other contents (hereinafter referred to as "primary contents") being displayed on a first portion 205 of the first display 201. Additionally, the first display 201 may display a time line 206 which corresponds to the contents displayed in the first portion 205. Additionally, a second portion 207 of the first display 201 may provide a quick key to jump to various portions within the primary contents displayed in the first portion 205. The quick keys may vary according to size and indexing of the primary contents or may be custom partitioned or set by the user. In an exemplary embodiment, the captured contents is part of communication data obtained in real time, which may be reviewed at a later time and additional text input maybe provided in the obtained communication data, as explained in further detail below.

Additional contents (hereinafter referred to as "secondary contents") related to the primary contents may be provided on a second display 202. This is provided by way of an example and not by way of a limitation. The second display 202 may display scripts (converted text of the primary contents) which are synchronized in real time with actual portions of the primary contents being displayed. Additionally, the second display 202 may display notes related to the primary contents as previously captured by the user and/or other users or is currently added by the user and/or other users. The second display 202 may provide functionalities available with respect to the secondary contents such as search, edit, delete, save, and add. The second display 202 may also provide icons related to other applications available in the apparatus 100, explained in further detail below according to various exemplary embodiments. The second display 202 may further provide a color-coded timeline 207 in which cognitive data (user's emotions) are color coded with respect to time.

Additionally, according to an exemplary embodiment, captured cognitive or emotional state of a user of the apparatus (hereinafter referred to "cognitive contents") may also be provided on the first display 201 but is not limited thereto. The cognitive or emotional state of the user may be provided on the second display 202 or on both displays 201 and 202 in various forms, as described in greater detail below according to various exemplary embodiments.

Figure 3C:
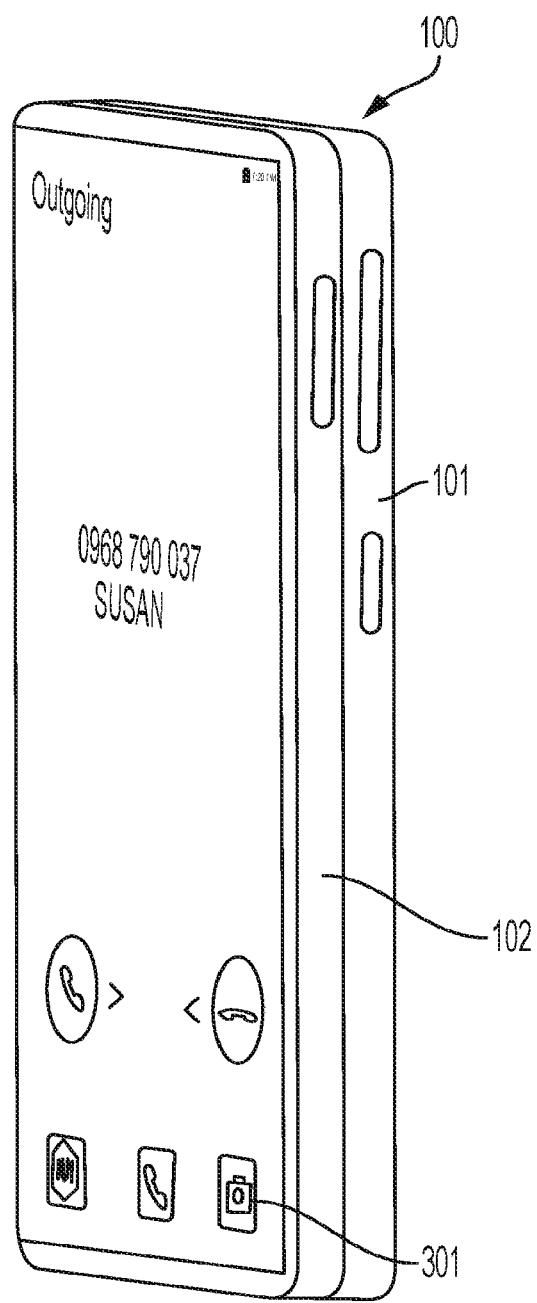
FIGS. 3C and 3D are views illustrating a front side and a back side, respectively, of an apparatus in a fully open state, according to an exemplary embodiment.
Figure 3D:
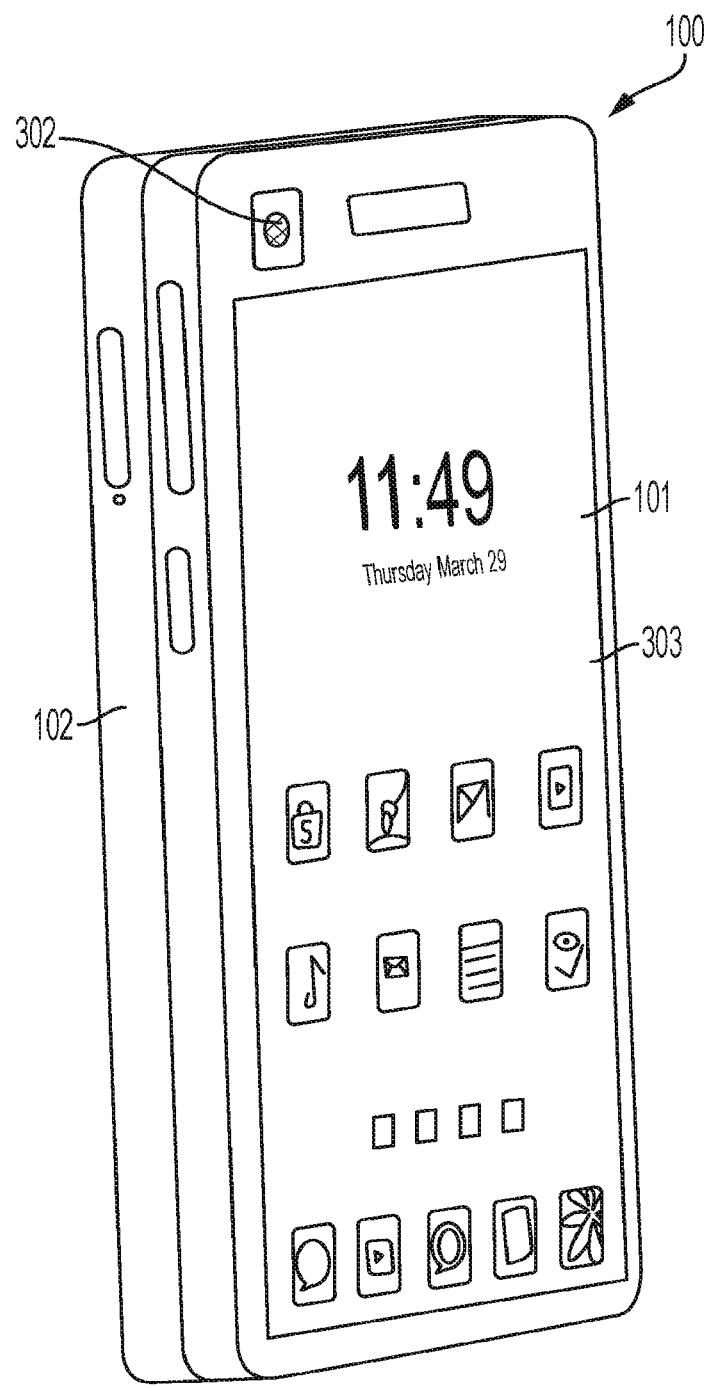

FIGS. 3C and 3D are views illustrating the apparatus 100 in a fully open state (360 degree open) according to an exemplary embodiment. In this open state, the front side is the second part 102 and may display a camera icon 301 (shown in FIG. 3C) to capture the environment with the camera 302 (shown in FIG. 3D). In an exemplary embodiment, icons of various functions and/or applications executable by the apparatus may be displayed on the first part 101 (which is referred to as a back display 303, shown in FIG. 3D) or on the front display of the second part 102 (shown in FIG. 3C). FIG. 3C shows the front display (second part 102) displaying that the apparatus is entering a communication mode in which a telephone call or a video call is being made to another user ("Susan"), according to an exemplary embodiment. The communication mode is explained in further detail below according to various exemplary embodiments. When the apparatus is open 360 degrees (FIGS. 3C and 3D), the device may be working the same as other smart phones known in the art. The camera 302 is on an internal side of the first part 101 and faces the environment when the apparatus is in an open 360 degrees state and an internal side of the second part 102 faces the user. If the user want to take a photo, he or she just touches an icon displayed on the internal side of the second part 102 in an analogous ways as using other smart phones and is known in the art, according to an exemplary embodiment. In an exemplary embodiment, the environment of the user may be captured with the camera 302 and/or shared during a communication using the first part 101, as explained in greater detail below according to various exemplary embodiments.

According to an exemplary embodiment, in the 360 degree open state of the apparatus 100, the internal side of the second part 102 becomes the front side that faces the user and that is being observed and manipulated by the user and the internal side of the first part 101 becomes the back side that faces the environment of the user to capture images and/or video of the environment, provide audio and visual output to the environment (such as a flashlight functionality). These are provided by way of an example and not by way of a limitation. According to an exemplary embodiment, the user may flip the phone so that the first part 101 faces the user and select some of the applications available on the first part 101.

FIG. 3C shows that the user of the apparatus, Mary, is making a call to her friend Susan. FIG. 3C shows the apparatus 100 entering a communication mode, as explained in further detail below according to various exemplary embodiments.

Figure 4:
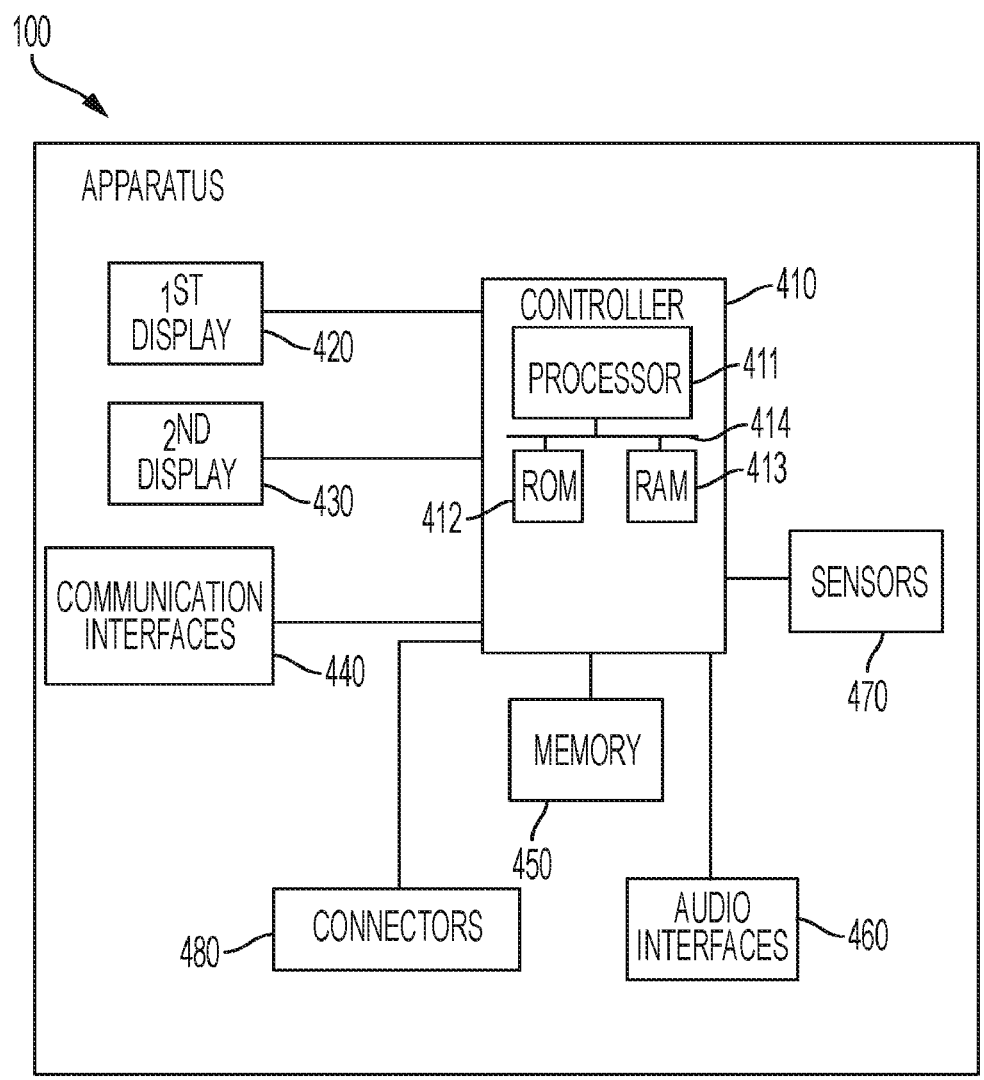
FIG. 4 is a block diagram illustrating a hardware configuration of an apparatus providing cognitive assistance for communication according to an exemplary embodiment.

FIG. 4 is a block diagram illustrating a hardware configuration of an apparatus providing cognitive assistance for communication according to an exemplary embodiment.

In FIG. 4, the apparatus 100 has a controller 410, a first display 420 and a second display 430, communication interfaces 440, a memory 450, audio interfaces 460, sensors 470, and connectors 480. These are provided by way of an example only and not by way of a limitation. One of ordinary skill in the art would readily appreciate that a smart phone may include a variety of these hardware components and other hardware components in various combinations.

The controller 410 may include at least one processor 411 including two graphical processors (GPU). One GPU may be provided for each display. The one or more processor 411 may further include a central processing unit (CPU), a video processor, an audio processor, a random access memory (RAM) 412 which stores signals external to the apparatus 100 or various instructions and operations to be executed by the apparatus 100, a read-only memory (ROM) 412 in which a control program such as an operating system software is stored to control functions of the display apparatus. The components of the controller 410 are connected to each other via an internal bus 414. The controller 410 controls the components of the apparatus 100. The controller may further include interfaces (not shown) to communicate with various internal components. Additionally, at least some of the components explained above may be provided on a separate chip and not be a part of the controller. For example, a video and/or audio processor may be provided as separate hardware components.

The first display 420 and a second display 430 may display first, second, and cognitive contents, as explained in further detail below. Additionally the displays 420 and 430 may be a touch screen such as to receive user input via touch.

The communication interfaces 440 may receive and transmit signals and/or data from the outside (including external devices and/or servers). For example, the communication interfaces 440 may include a network card and other hardware components in combination with software that provide for a wireless local rear network (WLAN) communication, Bluetooth communication, short-range communication, cellular communication, and data network communication, as may readily be understood by one versed in the art. For example, when the apparatus 100 enters into the communication mode, signals from one or more other apparatus are received via one or more of the communication interfaces 440.

A memory 450 may include an internal memory of the apparatus 100, which may store primary, secondary, and cognitive contents. The memory 450 may include a hard disk, a memory card, a secure digital card, a smart card such as a SIM card, and so on. These are provided by way of an example and not by way of a limitation. Additionally, the apparatus 100 may communicate with a cloud server (not shown) and obtain contents from the cloud server.

The audio interfaces 460 may include one or more audio output interfaces such as one or more speakers and a headphone socket to provide an audio output to headphones. The audio interfaces 460 may further include one or more audio input interfaces such as a microphone. These are provided by way of an example and not by way of a limitation. For example, during the communication of the apparatus 100, audio data may be captured via the audio interfaces 460 and may also be output via the audio interfaces 460 under the control of the controller 410.

The sensors 470 may include a camera and one or more of optical sensors, distance and pressure sensors such as the ones that capture change in the flow of electricity on a touch screen, and motion sensors, as would be readily appreciated by one of ordinary skill in the art. These are provided by way of an example and not by way of a limitation.

The connectors 480 may include a USB port connector for communicating data to and from another device, a power supply connector, and so on, as would be readily apparent to one versed in the art. These are provided by way of an example and not by way of a limitation.

Figure 5A:
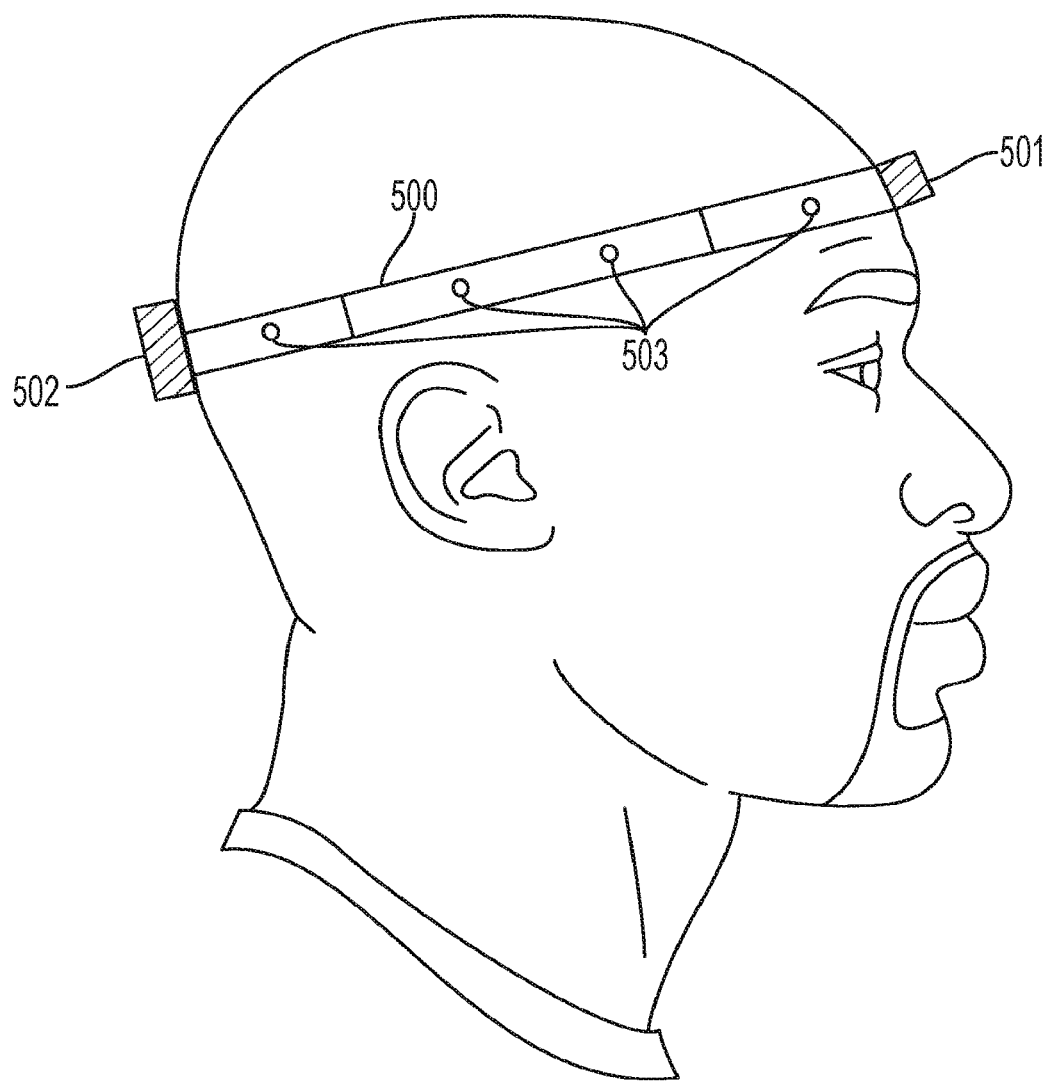
FIGS. 5A-5C are views illustrating various devices which capture cognitive states sensory data, according to exemplary embodiments, and illustrate synchronized cognitive states sensory data captured by various devices and interpreted to correspond to a classified cognitive state of a user, according to exemplary embodiments.
Figure 5B:
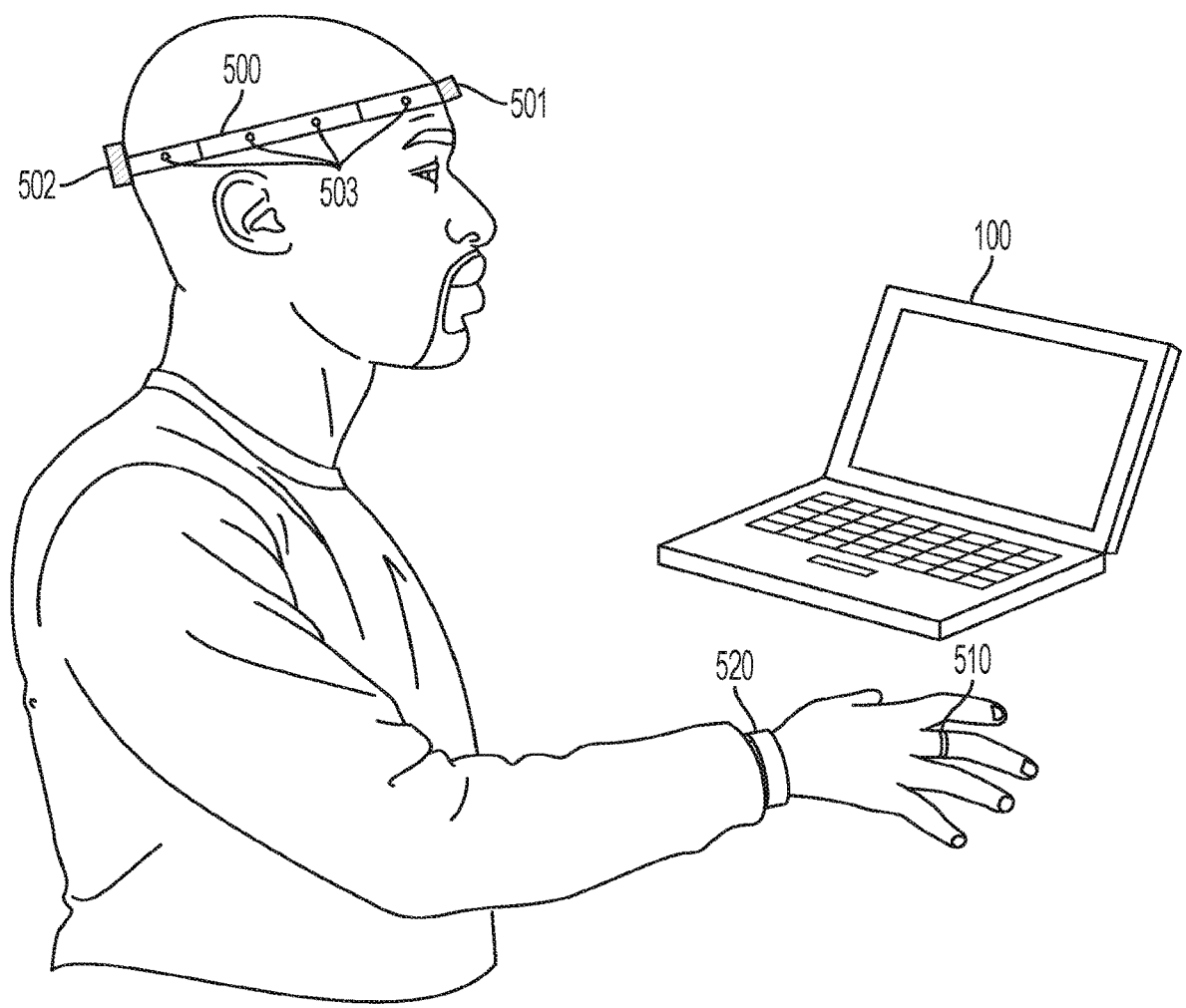
Figure 5C:
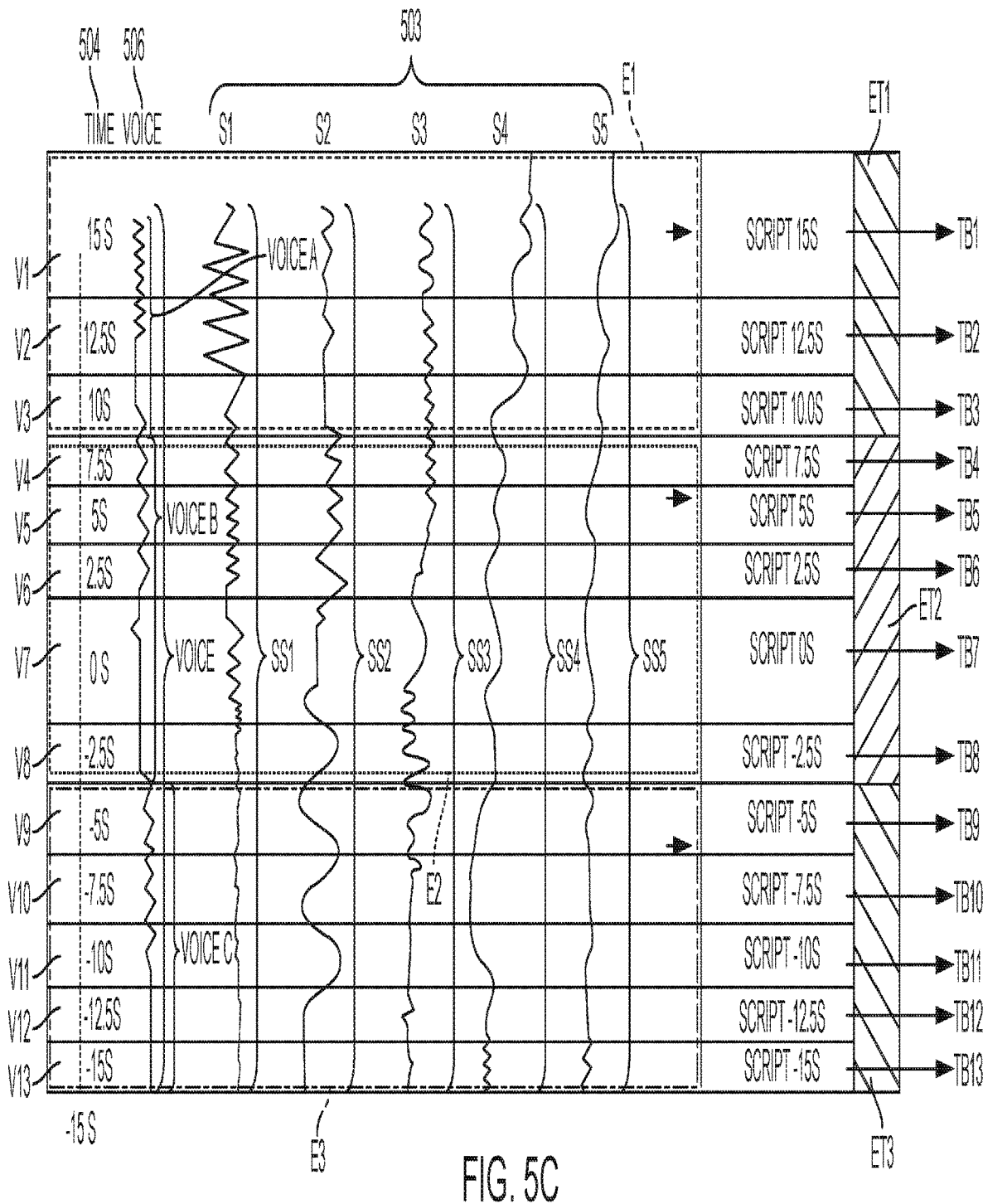

FIGS. 5A-5C are views illustrating a device which captures supporting communication contents and sensory data including cognitive and emotional data, according to an exemplary embodiment, and illustrating cognitive and emotional data captured by the device and interpreted to correspond to a classified cognitive and emotional state data of a user, according to an exemplary embodiment.

In an exemplary embodiment, two types of memory that the brain is working with during communication are imitated. Type one is a declarative memory or an explicit memory related to events, facts, thoughts, people, objects, and places that are addressed during a conversation. That is, elements or objects that are discussed or come up in a communication. Type two is a non-declarative memory, procedural memory, or implicit memory related to skills, habits, and natural reactions in a communication. That is, emotions or reactions to objects or elements that comes up during the communication.

In an exemplary embodiment, cognitive data is captured from the brainwave or other physiological signals generated when the brain is working with the type one memory (explicit memory). Additionally, emotional data is captured from brainwave or other physiological signals generated when the brain is working with the type two memory i.e., implicit memory.

As illustrated in FIG. 5A, a camera 501, which includes a microphone, may be provided on a front portion of the headset 500, according to an exemplary embodiment. This is provided by way of an example and not by way of a limitation. Multiple cameras may be provided such as a left camera, a front camera, a right camera, and a back camera to capture visual data and/or audio data according to an exemplary embodiment. One of ordinary skill in the art would readily appreciate that visual data and/or audio data may be captured with a personal device such as a user's personal data assistant or a cellular telephone. The captured visual and audio data (VI) may then be transferred to an electronic circuit board 502, which includes at least a memory coupled with a processor.

In an exemplary embodiment, the electronic circuit board 502 may process sensory data to generate cognitive and emotional state of a user. In yet another exemplary embodiment, the generated cognitive and emotional state information may be transmitted to another remote device for storage, monitoring, or further processing via a communication interface (not shown) provided on the headset 500. For example, the headset 500 may include a communication interface (e.g., a network card, an antenna, and other interfaces known to one of ordinary skill in the art or later developed) to transmit the data wirelessly e.g., a Bluetooth, Infrared, WiFi, and/or a cellular network to a remote server or a cloud for further storage, processing or monitoring and co-supervising. The communication interface may be built into the electronic circuit board 502, may be built into the communication device 100, or may be provided as a separate device on the headset 500. According to an exemplary embodiment, a USB port may be provided on the electronic circuit board 502 or separately on the headset 500 so as to plug into a computer to transfer captured data (VI data and sensory data).

In an exemplary embodiment, one or more emotional sensors or cognitive state sensors 503 are further provided on a headset 500. While FIG. 5A depicts four cognitive state sensors 503, this is provided by way of an example and not by way of a limitation. One of ordinary skill in the art would readily appreciate that a single sensory or cognitive state sensor may be used but preferably multiple cognitive state sensors are provided to capture cognitive state of a user. The cognitive state sensors 503 may be provided on both sides of the headset 500. In an exemplary embodiment depicted in FIG. 5A, only one side of the user's head is shown but the other side may also include four cognitive state sensors 503 that detect the cognitive state of the user. That is, in an exemplary embodiment, cognitive state is obtained from multiple sensors 503 by detecting activities in various parts of the brain.

FIG. 5B is a view illustrating another apparatus which captures supporting communication contents and sensory data including cognitive and emotional data, according to an exemplary embodiment. As shown in FIG. 5B, a device 510 may be worn on a finger of a user and capture emotional states of the user during a conversation, according to an exemplary embodiment. The device 510 captures emotional states of the user through physiological signals by measuring Heart Rate (HR), by way of an example.

According to an exemplary embodiment, FIG. 5B may also include another device 520 worn on the hand of the user similar to a watch. This other device 520 captures emotional states of the user during a conversation. The another device 520 captures emotional states of the user through physiological signals by measuring items like blood volume pulse (BVP), skin temperature (SKT), by way of an example and not by way of a limitation.

According to an exemplary embodiment, EEG and other physiological signals such as HR, BVP, SKT are provided by way of an example and not by way of a limitation.

Figure 6:
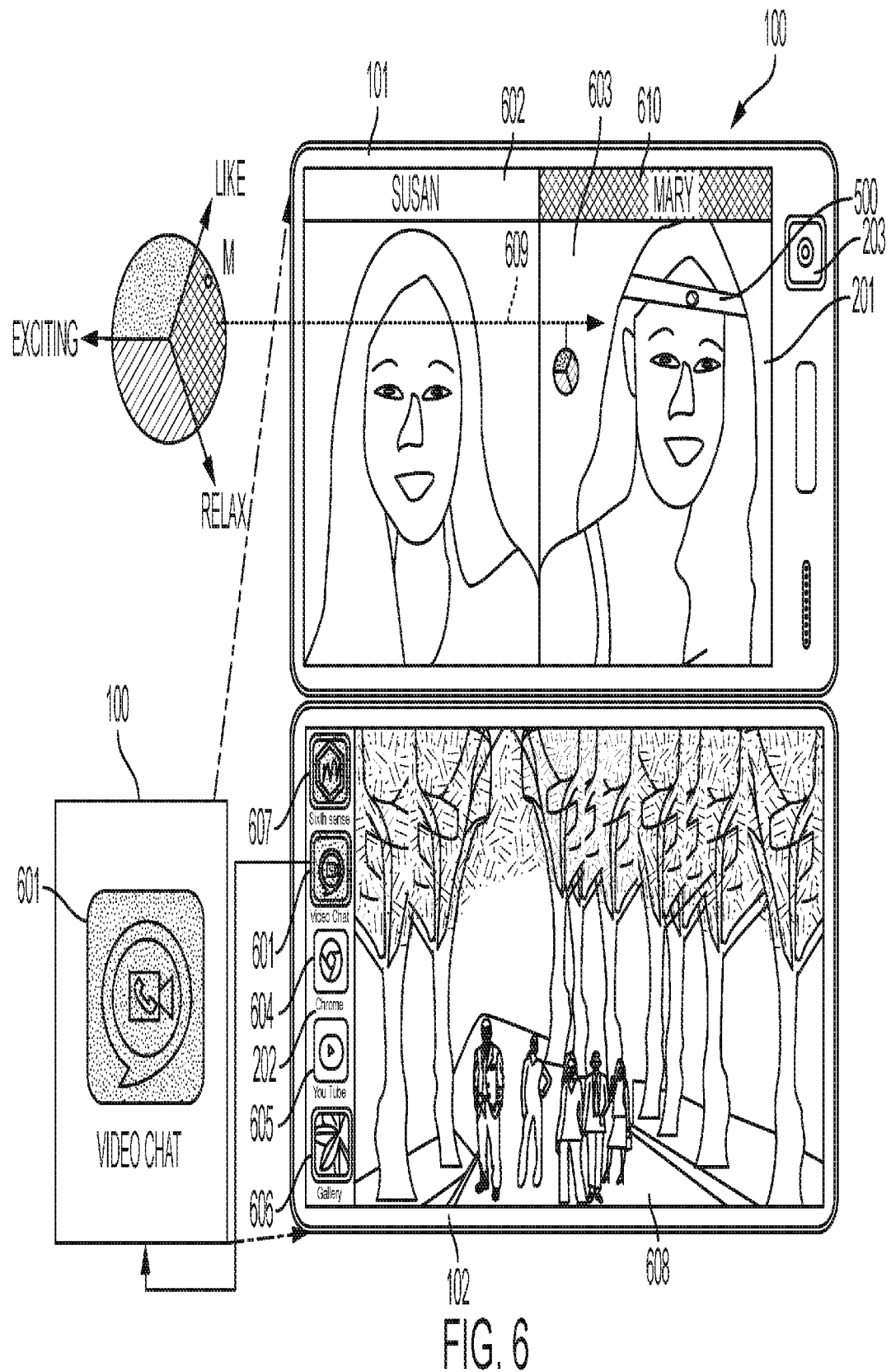
FIG. 6 is a view illustrating an apparatus providing an emotional state of a user while being in a communication mode, according to an exemplary embodiment

According to an exemplary embodiment depicted in FIG. 5B, the user may be using the apparatus 100 with his or her hands while wearing the device 500. For example, as explained in further detail below, the user may be looking in front of her while walking on a path in an alley with Sakura trees on both sides of the alley, as shown in FIG. 6. The user may be talking with friend (Susan) about the event which is live streaming with her devices.

According to an exemplary embodiment, as shown in FIG. 5B, the user is using apparatus 100 while wearing at least one of the devices 500, 510, and 520. According to an exemplary embodiment, explained below with reference to FIG. 6, the user may be looking in front of him or her at the device, which displays people walking in an alley in a park. The user may be talking to a friend about the event which is live streaming with her devices. The devices 500, 510, and 520 will capture physiological data, according to an exemplary embodiment.

According to an exemplary embodiment, raw sensory signals obtained from the sensors are combined and synchronized with the communication. In an exemplary embodiment, the raw signals embody sensory distinctive instinct components. In an exemplary embodiment, raw sensory signals are filtered at distinctive reference signals to detect ET1 component for the levels of loving state where a user is instinctively engaged and attracted (excited, loved) during the conversation, ET2 component for the levels of liking state where a user is consciously (or rationally—please recommend which one is used better) engaged and persuaded (liking) during the conversation, and ET3 component for the bored state where a user is feeling bored or not-engaged during the conversation, as shown in FIG. 5C and explained in greater detail below.

According to an exemplary embodiment, ET1 indicates the emotional states at a very high level, ET2 indicates both emotional and cognitive states at rather high levels, ET3 indicates a low level of both emotional and cognitive states, as shown in FIG. 5C.

According to an exemplary embodiment, when the discrimination between certain sensory signals' components and referenced signals are increased or decreased means that the user is at an identified level of an identified state such as excited (very interested, naturally attracted and engaged), liking (rationally engaged and persuaded, good feeling, like), and so on. For some examples, see U.S. Pat. No. 9,711,056 and U.S. patent application Ser. No. 15/870,210 filed on Jan. 12, 2018, which are incorporated herein by reference in their entireties.

According to an exemplary embodiment, the cognitive state sensors 503 may be positioned to detect levels of main emotions of the user such as liking, loving and exciting, or boring. For example, as shown in FIGS. 5A and 5B, four sensors 503 (S1-S4) are placed on head of the user and output respective sensory signals ss1-ss4 and one emotional sensor S5 is placed on the other part of the body of a user such as an apparatus 510 and/or 520. In an exemplary embodiment, if the ET 1 signals detected from sensors S5 output respective signals above predetermined respective values, a determination can be made that the user feels very excited e.g., the user is highly engaged in the communication and the communication is stimulating instinctive interests to the user. If the detected ET 2 signals from sensors S1, S3, output respective signals above predetermined respective values, a determination can be made that the user feel that he is engaged and liking or feeling good about the conversation. If the detected ET 3 signals from sensors S2, S4, output respective signals under predetermined respective values, a determination can be made that the user feels that he is not engaged and bored with the conversation.

In an exemplary embodiment, because the user reads text from top to bottom (i.e., from the upper line to the lower line), therefore signals of voice which are interpreted synchronously with the text lines. As such, in an exemplary embodiment depicted in FIG. 5C, audio signals i.e., voice output, is displayed in a vertical line(s) and the timeline is also displayed in a vertical direction, for consistency with the text.

FIG. 5C, according to an exemplary embodiment, depicts voice signals captured for an episode of 30 seconds. For example, a timeline 504 is depicted on the left side of FIG. 5C and is split into 13 intervals depicted by 2.5 seconds for each interval. The 5 seconds mark depicts voice data already spoken by the user and/or the other user of the conversation and the −5 seconds mark depicts voice data to be spoken by the user and/or the other user of the conversation in 5 seconds (if the conversation has been recorded and is being played back by the user). 0 seconds mark indicates the current position of the voice data being output. According to an exemplary embodiment, 0 seconds indicate the voice data and visual data currently being presented during a video conference or a teleconference between a user and another user.

According to an exemplary embodiment, the first voice A of a first user may be captured during time intervals V1-V3, a second voice B of another user may be captured during time intervals V3-V8, and the third voice C of the first user may be captured during the time intervals V9-V13. These are provided by way of an example only and not by way of a limitation. The captured voices are split into voice segments. Based on the split voice modules or segments V1, V2, . . . V13, voice to text conversion is performed. That is, voice data is converted into text data and may be displayed to the user, as explained in greater detail below. In an exemplary embodiment, one text box is provided for each voice segment or module. For example, as depicted in FIG. 5C, the text, obtained from converting the voice signal, is displayed in respective text boxes TB1-TB13. That is, the first text corresponding to the converted voice segment V1, is displayed in the text box TB1; the second text corresponding to the converted voice segment V2, is displayed in the text box TB2; and the 12$^{th}$ text corresponding to the converted voice segment V12, is displayed in the text box TB12.

In an exemplary embodiment, the text output corresponding to the converted voice is placed into 13 corresponding script lines, which are TB1, TB2, . . . TB13 and script (−15$_s$), script (−12.5$_s$) . . . script (15$_s$) depicted in FIG. 5C. In an exemplary embodiment, the number of sub-windows being displayed will correspond to the number of voice segments generated during the division of continuous voice output. As shown in FIG. 5C, cognitive state of the user is also displayed as five emotional state signals ss1-ss5 obtained from the sensors S1, S2 . . . S5. These cognitive state signals are also displayed synchronized with voice signal in the vertical direction. According to an exemplary embodiment, the cognitive state signals ss1-ss5 are also split into segments corresponding to the voice segments V1-V13. That is, in an exemplary embodiment, the emotional state signals are analyzed in segments which correspond to the voice segments to determine an emotional state of the user.

As shown in FIG. 5C, E1 is an emotional state obtained from analyzing of at least one of signals ss1, ss2, ss3, ss4, and ss5 produced at time 15 sec to 10 sec and corresponding to the voice segment V1 to V4, the text of which is displayed in the TB1 to TB4 box. In an exemplary embodiment, E3 is interpreted to correspond to an emotional state 3 and can be marked with a first color (e.g., blue) to indicate that the user is bored, not engaged (or neutral emotion) about the conversation corresponding to the voice segment V8 to V13 . That is, E3 indicates a state in which the user is feeling bored about the contents of the voice segment V8-V13. E2 is the cognitive state obtained from at least one of signals ss1-ss5 recorded during the conversation from V5 to V7 with content displayed in TB5 to TB7. E2 is interpreted to correspond to an emotional state 2 and can be marked with a second color (e.g., green) to indicate that the user is enjoying or liking the contents presented (voice segment V5-V7) and visual contents). E1 is the emotional state obtained from at least one of signals ss1-ss5 recorded during the time the user hears voice V1 to V4 with content displayed in TB1 to TB4. E1 is interpreted to correspond to an emotional state 1 and can be marked with a third color (e.g., red) to indicate that the user is excited about the contents (voice segment V1 to V4 and visual contents). The marking depicted in FIG. 5C are provided by way of an example and not by way of a limitation. According to another exemplary embodiment, the text in the respective text boxes TB1-TB13 can be color coded based on the determined emotional state (E1-E3) of the user.

As an alternative, various marking and indicators could be used to depict the user's state including % level of each color, mixing 3 colors R (red), G (green), and B (blue) to reflect a general emotional state of the user during the conversation in real time, as explained in further detail with reference to FIGS. 6 through 13.

According to an exemplary embodiment, the voice signal 506 may be a voice of the user and/or another user during a teleconference, a video conference, or a gaming session, for example. Contents shared during the video conference maybe recorded as visual data and stored in synchronization with the audio signals output by the users, for example.

According to an exemplary embodiment, the memory of the electronic circuit board 502 may store captured primary data (including the captured video data and audio data) and the captured sensory data, which may be the EEG or other physiological signals, explained above. The processor of the electronic circuit board 502 may execute a synchronizer, which is configured to synchronize the captured primary data with the captured sensory data, by way of an example. At this point, the processor of the electronic circuit board 502 may transmit the synchronized data modules including the primary data with the corresponding sensory data to another processor or a server for further processing via the communication interface of the electronic circuit board 502. According to another exemplary embodiment, the processor of the electronic circuit board 502 may execute an emotional state determiner, which determines the emotional state of the user ET1-ET3. According to an exemplary embodiment, the processor of the electronic circuit board 502 may determine the emotional state of the user based on the sensory data provided by the emotional state signals SS1-SS5 at time t0 corresponding to the primary data at time t0. Additionally, the processor may convert an audio part of the primary content (user voices during the teleconference or videoconference) to text via a speech to text converter executed by the processor of the electronic circuit board 502 or executed by a remote server or computer. Next, a script generator, executed by the processor of the electronic circuit board, generates scripts of the audio contents. Additionally, the script generator may generate a plurality of text boxes for the segmented scripts and color code the text boxes (by way of an example) based on the sensory data using the output from the synchronizer, the emotional state determiner, and the speech to text converter. The primary contents, along with the emotional states may be output to a user via one of the displays of the apparatus 100.

As shown in FIG. 3C, discussed above, the apparatus 100 is entering into a video conference mode according to an exemplary embodiment. As shown in FIG. 3C, a user named Mary is calling her friend Susan. Mary is wearing I SEE® headset (the headset 500) that detects and monitors her emotional and/or cognitive state, which she may view herself and/or decide to share with her friend Susan via one of the displays of her apparatus 100, as explained in further detail below.

FIG. 6 is a view illustrating the apparatus 100 in a communication mode, according to an exemplary embodiment. As shown in FIG. 6, Mary and Susan are using video chat executed via a selection of an icon 601. Mary is traveling to see the Sakura trees in Japan in spring and livestream chatting with Susan about what she is seeing and feeling in Japan. That is, when Mary selects an icon 601, as is known in the art or later discovered, the apparatus 100 transitions into the communication mode in which a video conference is conducted. According to an exemplary embodiment, the apparatus enters into a communication mode once a connection is established with another user, Susan, as shown in FIG. 6.

According to an exemplary embodiment, the apparatus 100 may record audio and visual data of the communication such that the headset 500 captures the cognitive or sensory data and also the visual and audio of the environment that user, Mary, is in. The communication data may be synchronized with sensory data via a world-time clock signal for example. According to another exemplary embodiment, the headset 500 only captures the user's emotional and cognitive data in addition to the sensory data and other components of the apparatus 100 captures the visual and audio of the environment such as a camera 203.

As shown in FIG. 6, the first part 101 of the apparatus 100 has a first display 201 and a camera 203. The camera 203 is configured to capture Mary in real time during her communication with Susan and is shown as enable on the first display 201. According to an exemplary embodiment, the camera 203 provides video conferencing functionality to display the primary contents (video and audio captured by the camera 203 and/or microphone). The display 201 is split into two portions, a first screen 602 and a second screen 603. The first screen 602 displays Susan in real-time and the second screen 603 depicts Mary, the user of the apparatus 100, in real time. Mary is wearing the I SEE® headset 500 to determine her emotional or cognitive state and capture video of what she is seeing and talking about. In an exemplary embodiment depicted in FIG. 6, a video chat is conducted between Mary (hereinafter referred to as a user), and Susan (hereinafter referred to other entity). These are provided by way of an example and not by way of a limitation.

According to an exemplary embodiment depicted in FIG. 6, Mary is telling a live event to Susan. The visual and audio data captured by the apparatus 100 is referred to as primary data (communication data) and is displayed on the first display 201. As is known in the art, the video and/or audio data of the user is shared with the other entity, Susan.

The visual and audio data captured by the headset 500 is referred to as live streaming data (live environment data) and is displayed on the second display 202. As is known in the art, the video and/or audio data of the user is shared with the other entity, Susan. In an exemplary embodiment, in addition to viewing Mary during the video chat, Susan is also provided with Mary's environment i.e., the path in the park on which Mary is currently walking.

Mary also may wish to show additional contents (such as other images, videos, websites, photos, text documents, and so on). Accordingly, Mary may select one of the icons displayed on the second display 202 of the second part 102 of the apparatus 100 to share additional contents.

As shown in FIG. 6, other applications may be accessed from the video conference according to an exemplary embodiment. For example, the user may select an icon 604 to obtain contents from Internet for the sharing during the video conference. The user may select an icon 605 to obtain video contents from a YouTube (video Internet source) for the sharing. The user may select a gallery icon 606 to obtain images and/or videos stored by the apparatus 100 for the sharing. The selected image will be displayed in a third screen 608 of the second display 202 indicated as shared. That is, according to an exemplary embodiment, the third screen 608 is displayed by the apparatus 100 to the user as the content selected and shared with the other entity, Susan. As shown in FIG. 6, the gallery icon 606 is selected and the gallery application is executed from the video chat 601 and the additional image selected via the gallery application is displayed in the third screen 608, as being shared by the user. These are provided by way of an example only and not by way of a limitation.

According to an exemplary embodiment, the third screen 608 may display current video contents captured by the device 500 (Mary's live environment data) or may be replaced by an image selected from a gallery 606, for example. According to yet another exemplary embodiment, the third screen 608 may be split into two sub screens such that first sub screen plays Mary's live environment data and a second sub screen depicts additional contents selected via various applications available to the display apparatus.

As shown in FIG. 6, the video chat icon 601 may be shown as enabled to indicate that a video conference is currently occurring. Additionally, the gallery icon 606 is shown as enable to indicate that the additional image displayed in the third screen 608 and shared during the video conference is from the enabled gallery application.

According to an exemplary embodiment depicted in FIG. 6, the user, Mary, may also select a FUVI icon 607 while in the apparatus 100 is in the communication mode. That is, the user may select the Fuvi icon 607 from within conducting the video chat 601. According to an exemplary embodiment, when the Fuvi icon 607 is enabled, the Fuvi icon is indicated as enabled on the second display 102 and a corresponding sixth sense application is executed to capture the emotional state of the user. The sixth sense application executed by the apparatus 100 sends a start signal to the headset 500 indicating that the headset 500 should capture the live streaming video (live environment data) and the corresponding sensory data. In response to receiving a start signal from the apparatus 100, the headset 500 begins capturing environment data in synchronization with the emotional sensory data.

According to an exemplary embodiment, the headset 500 may broadcast the captured live environment video and sensory data in real time with the apparatus 100 and the sixth sense application being executed on the apparatus 100 may execute the emotional state determiner, the speech to text converter, and the script generator, explained above with reference to FIGS. 5A-5C. According to yet another exemplary embodiment, the headset 500 may execute the state determiner, the speech to text converter, and the script generator. According to yet another exemplary embodiment, the headset 500 may communicate with an external server to obtain the text blocks and the emotional state of the user and communicate the same to the apparatus 100. The sixth sense application then displays the emotional state 610 of the user, Mary, in real time during the video communication.

That is, according to an exemplary embodiment, the second screen 603 may be color coded in real time based on current cognitive or emotional state of the user (Mary) as captured by the headset 500. A cognitive map or key of emotional states 609 may also be displayed in the second screen 603, color-coded to show various emotions. This is provided by way of an example and not by way of a limitation. According to yet another exemplary embodiment, not to obscure the third screen 603, the emotional state of the user may be displayed color coded and as text 610 in the third screen 603.

According to an exemplary embodiment, the emotional state of the user may be shared with the other entity. That is, the user may decide to share her emotional state with the other entity. As such, the other entity, Susan, not only obtains the video of Mary in real time and the additional contents being shared via the third screen 608 but also Mary's actual emotional state 610. That is, although the user may be smiling, the other entity would know that the user is feeling sad or upset and the smile is a fake smile based on the emotional state captured by the headset 500. Similarly, even if the emotional state of the user is not being shared, the user herself may realize her emotional state. For example, the user may be sharing a memory with Susan saying how much she hated her trip to the park but her emotional state may actually indicate that she liked the trip to the park. As such, the user knows her actual state as the memory or story is being shared.

According to an exemplary embodiment, the other entity, Susan, may understand the user of the apparatus not only based on audio/video/and additional contents being shared during the video conference but also based on the cognitive or emotional state of the user. For example, Susan may show the user a new dress she just purchased as additional contents in the third screen 608 and as the user is saying how cute the dress is, the other entity may also see the user's emotional state as like and know, with certainty, that the user actually likes the dress and is not just saying this. As such, the user and the other entity may communicate not only in real time with additional contents being shared but by also sharing the emotional state of the user to enhance the communication. The emotional states are a spectrum, as shown in the color coded key 609, where green is like, yellow is between like and excited, red is excited, purple is dislike, and blue is relaxed.

In an exemplary embodiment, I SEE® headset 500 is used to detect (filter) emotional data and divide it into 3 components (from 3 different bands), according to an exemplary embodiment. Three bands are provided by way of an example and not by way of a limitation. According to an exemplary embodiment, a first band is represented by R (red color %), a second band is represented by G (green color %), and a third band is represented by B (blue color %). By mixing these 3 colors with its real-time percentage, different colors are obtained, which reflect user's emotional states in real-time. In an exemplary embodiment, the green color (third band) relates to "like" state of the user. That is, the user likes what he or she is seeing (pleasant emotions). The red color (first band) represent "exciting" state and may relate to "love". The blue color (second band) relates to a "relaxed" state. As a result, for example, a purple color (which would be a combination of blue and green, a predetermined percentage of the two) may be related to bored and/or sleepy. In an exemplary embodiment, mixed percentages of these three bands represent a different state of the user analogously to mixing various colors. In an exemplary embodiment, the principle is similar to color analyzing and processing for digital coloring.

Figure 7:
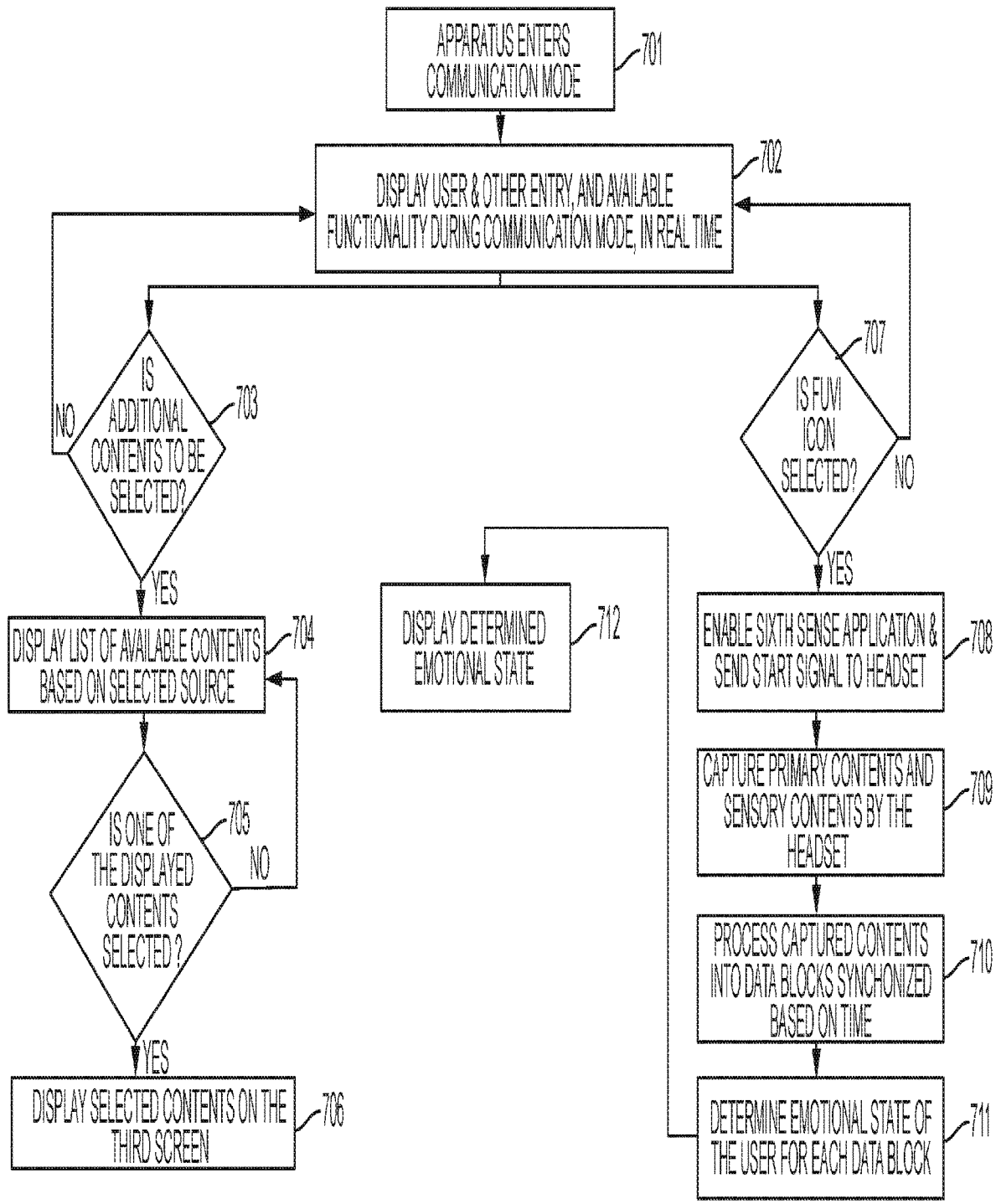
FIG. 7 is a flowchart illustrating a method of providing an emotional state of a user while an apparatus is in a commutation mode according to an exemplary embodiment.

FIG. 7 is a flowchart illustrating a method of providing an emotional state of a user while an apparatus is in a communication mode according to an exemplary embodiment.

In operation 701, the apparatus enters a communication mode. According to an exemplary embodiment, communication between a user of the apparatus and another entity is established e.g., a video conference, a virtual gaming session, or a teleconference. In operation 702, the first display of the apparatus displays the user in real-time and the other entity in real time, and the second display of the apparatus displays environment data in real time and various applications that may be selected while the apparatus is in communication mode. In an exemplary embodiment, the environmental data is video/audio data captured by the device 500 in real time. In an exemplary embodiment, the environmental data is environment observed by the user wearing the headset 500. In operation 703, the apparatus determines if a user selects one of the icons 601, 604, 605, and 606 to select additional contents to be displayed on the third screen 608 of the second display 102. If no, the method remains at operation 702 where the user and the entity are displayed in real time and the camera 203 and the video chat icon 601 are displayed as enabled. If the user selects one of the icons (Yes in operation 703), a list of available additional contents is provided to the user for a selection. That is, a source of the additional contents is selected in operation 703, a list, thumbnails, a search field, and other fields, as are known in the art, are provided to the user for a selection of additional content, in operation 704. In response to a user selecting one of the contents in operation 705, the selected content is displayed on the third screen 608 and is shared via a communicator with another apparatus of the other entity in the operation 706. Accordingly, as shown in FIG. 6, the user Mary and the other entity Susan are displayed on the first display 201 and the selected additional content is displayed on the second display 102. According to yet another exemplary embodiment, the content selected in operation 705 may be displayed on the third screen in operation 706 and may only be shared upon user confirmation. That is, the selected contents may be available for the user only and not shared with the other entity.

Additionally, the user may want to obtain her emotional state while the apparatus in in the communication mode. In operation 707, the user may select the FUVI icon from among the icons displayed on the second display 102. That is, the user may select sixth sense functionality from among a plurality of available functionalities displayed on the second display 102 while the apparatus is in a communication mode. In response to selecting to execute a sixth sense application in operation 707, the FUVI icon 607 (shown in FIG. 6) is displayed in an enabled state on the second display 102, in operation 708. Additionally, a start signal is communicated to a headset 500 (shown in FIG. 5A), in operation 708. In response to the start signal of the operation 708, the headset 500 may be paired to the apparatus 100 or it may have been paired to the apparatus 100 prior to the apparatus 100 entering the communication mode. In operation 709, the headset 500 starts recording audio and/or live streaming video (supporting communication contents) and capturing the sensory data (sensory contents) via the sensors 503 (shown in FIGS. 5A and 5B, for example). In operation 710, the captured supporting communication contents and sensory data are processed into data blocks in synchronization with each other based on world- clock time (by way of an example and not a limitation).

According to an exemplary embodiment, the headset 500 (shown in FIG. 5A) and/or other devices (shown in FIG. 5B) may capture in real-time audio and video contents. The video contents will include environment observed by the user which may be the two displays 201 and 202. That is, the visual contents will include an image of the user displayed in the second screen 603, an image of the other entity displayed in the first screen 602 and the image of the additional contents displayed in the third screen 608 and additional icons 601 and 604-607. According to an exemplary embodiment, the visual data of the additional icons may be discarded using image recognition techniques, known in the art. According to another exemplary embodiment, the images of the user displayed in the second screen 603 may also be discarded using image recognition techniques, known in the art. The captured primary contents (audio and video) that are not discarded may be recorded in data blocks e.g., 5 second intervals and stored by the headset 500 or transmitted to be stored to the apparatus 100 or an external server. The captured primary contents are synchronized with the sensory data. That is, sensory signals output by the sensors 503 for a predetermined time period e.g., 2.5 seconds interval, are captured and stored to determine the emotional state of the user. In an exemplary embodiment, the sensory signals may be stored in synchronization with the primary contents to form the data blocks. The headset 500 or the apparatus 100 may determine, in real-time, the emotional state of the user for a respective data block. The emotional state may then be displayed on one of the displays.

The data blocks are generated and stored by the headset 500 and/or the apparatus 100, for further analysis, as explained in further detail below. The determined emotional state is output in real time on one of the displays of the apparatus 100. The determined emotional state may be shared with the other entity or may remain private to be visible only to the user of the apparatus.

In an exemplary embodiment, the user may further select to display environment observed by the user and the environment observed by the user may then be displayed in real time in the third screen in a form of an image or video.

Figure 8:
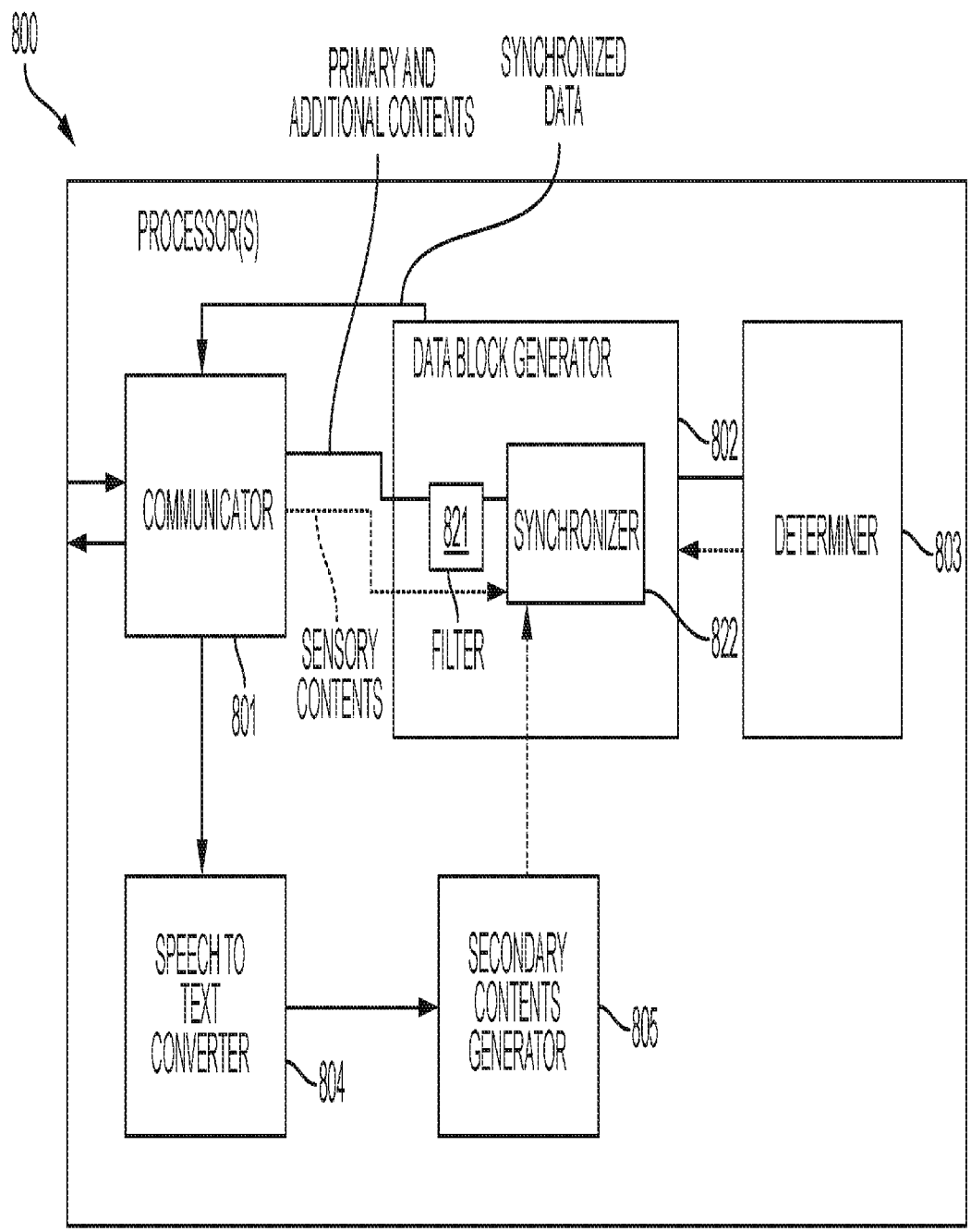
FIG. 8 is a block diagram illustrating components of generating data according to an exemplary embodiment.

According to an exemplary embodiment, primary data may be constructed into an episodic content scaffolds which may be embedded extending contents later. FIG. 8 is a block diagram illustrating components of generating data blocks according to an exemplary embodiment. As explained above in FIG. 5C, one or more processors such as the processor of the headset 500 together with the processor of the apparatus 100 and/or a processor of an external server(s) may generate data blocks according to an exemplary embodiment.

The processor 800 includes a communicator 801 configured to receive captured primary data, which may be audio and/or video and/or additional contents, as explained above and also configured to receive sensory data obtained from the sensors on a headset 500, as also explained above. The processor 800 may further include a data block generator 802, which is configured to generate data blocks. The data block generator 802 may include a filter 821, which discards portions of the primary data. For example, the filter 821 may discard the video data of the user of the apparatus 100. The filter 821 may also discard additional data based on user settings such as additional contents. The data block generator further includes a synchronizer 822, which synchronizes the remaining portion of the primary contents (as filtered by the filter 821) with sensory contents based on time to form a data block. For example, each generated data block includes the filtered primary data and the sensory data at time period t0-t1. The processor 800 may further include a determiner 803. The determiner 803 determines the emotional state of the user for each of the generated data blocks, as explained with reference to FIG. 5C. The determiner 803 may provide the determined emotional state of the user in real time via the communicator 801 to the displays of the apparatus 100. The determiner 803 may further provide the determined emotional state of the user to the data block generator to be added into the data block and the communicator 801 may transmit the formed data blocks to a memory for the storage.

The cognitive or emotional state of the user may be determined by the determiner 803 based on processed sensory data for each segmented portion of the data i.e., for each piece of contents, which is obtained in synchronization with the recorded audio/video data (primary contents) i.e., for each data blocks. When sensors on a certain part(s) of the brain output signals of a first amplitude (small amplitude) in one or more frequency bands, the determiner 803 may determine that the user is excited (confused, scared and/or concerned). On the other hand, when the sensors on another part of the brain output signals with a second amplitude (large amplitude), the apparatus may determine that the user is relaxed. According to an exemplary embodiment, signals with high amplitude in a first frequency band and low amplitude in a second frequency band may indicate an excited cognitive or emotional state of the user, whereas signal with low amplitude in the first frequency band and high amplitude in the second frequency band may indicate relaxed state of the user. If all of the sensors produce signals of the first amplitude, this may indicate that the user is asleep or not paying attention (very relaxed). This is provided by way of an example only and not by way of a limitation.

The processor 800 further includes a speech to text converter 804. The speech to text converter 804 may obtain only the audio portion of the primary contents via the communicator 801 (using an extractor, not shown) and convert the audio into text scripts. This is provided by way of an example and not by way of a limitation. According to an exemplary embodiment, the speech to text converter 804 may split the audio data (voice) into respective portions or chunks and convert to text, which is then displayed as scripts 91 (shown in FIG. 9, explained below). That is, the primary contents (video/audio data) are split into segments based on continuity of the voice signal via the speech to text converter. For example, a hardware processor of the apparatus 100 may determine where a pause is made or an end of a sentence based on voice intonation. According to an exemplary embodiment, equal length for a segment may also be set e.g., 2.5 seconds. This is provided by way of an example only and not by way of a limitation. That is, according to an exemplary embodiment, the size of the data block may be determined by the speech to text converter 804 and provided to the data block generator 802 via a second contents generator.

According to another exemplary embodiment, as shown in FIG. 8, the converted speech is provided to the secondary contents generator 805. The secondary contents are explained in greater detail below. The scripts, along with other secondary contents such as notes and comments may be provided to the data block generator to be added as part of the data block by the synchronizer 822. That is, the primary contents (audio/video data) is synchronized or linked with a corresponding determined cognitive or emotional state by the determiner 803 and (optionally) the segmented audio data which is converted into text by the speech to text converter 804 for a display on as scripts (shown in FIG. 9). The scripts may be generated in real-time as the conversation takes place. Each script may be displayed in a distinct manner (e.g., color coded) so as to show the emotional state of the user for each portion of the primary data.

Figure 9:
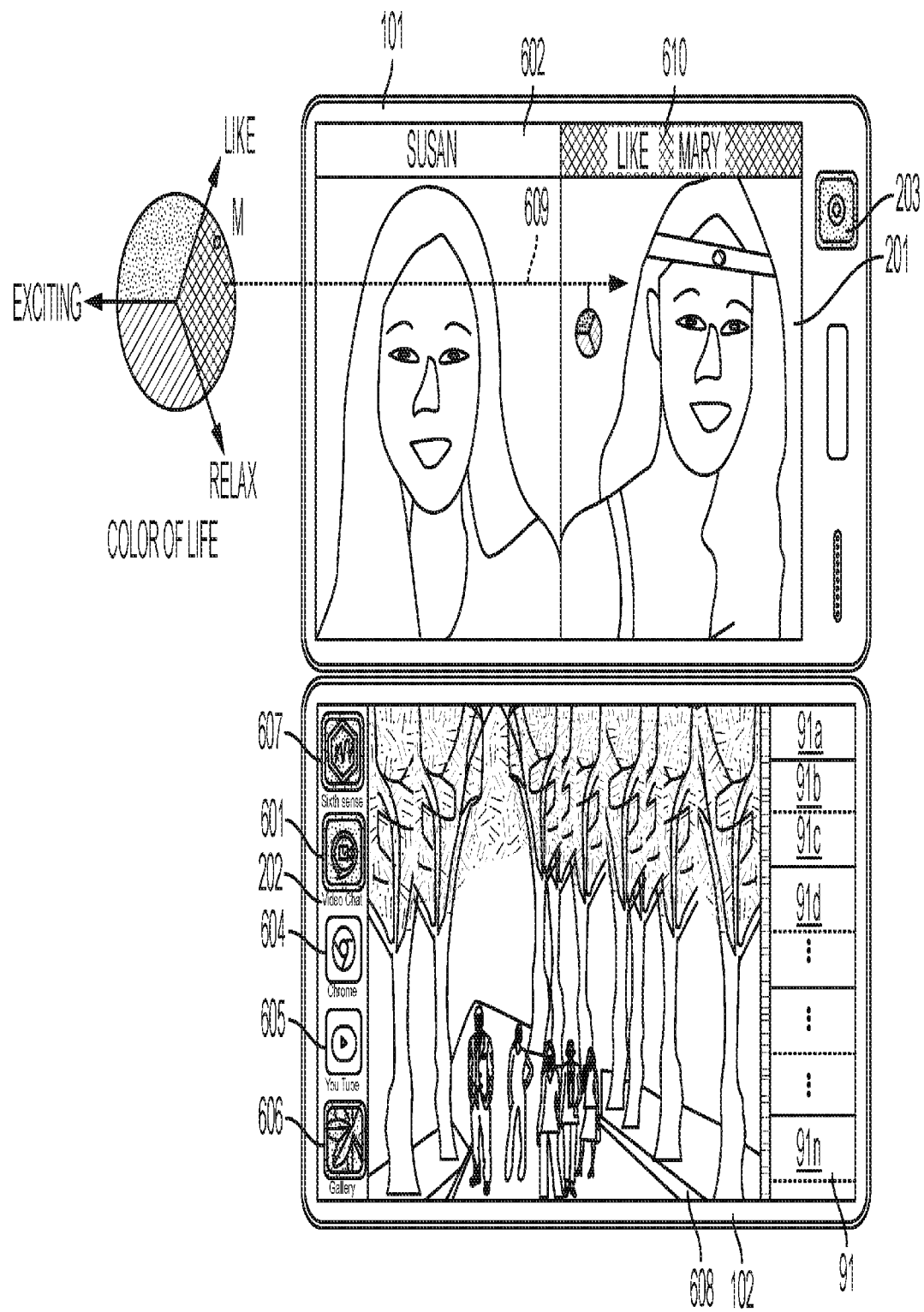
FIG. 9 is a view illustrating an apparatus providing secondary contents of a conversation and an emotion state of a user, while being in a communication mode, according to an exemplary embodiment.

FIG. 9 is a view illustrating an apparatus providing secondary contents of a conversation and an emotion state of a user, while being in a communication mode, according to an exemplary embodiment. According to an exemplary embodiment, based on a user input such as a swiping along the second display 102, the apparatus may further display secondary contents generated by the secondary content generator 805 of FIG. 8. The secondary contents include the scripts 91 of a conversation between the other entity Susan and the user Marry. The scripts 91 may be provided in text segments 91*a*-91*n* based on the data blocks generated by the data block generator 802 of FIG. 8. Additionally, each text segment may indicate whether the audio portion of the primary data belongs to the primary communication (live scripts) or the extended communication (later inputs) based on dotted line or solid line. Also, each text segment may be color coded based on the emotional state of the user as determined by the determiner 803. That is, user's emotional state with respect to each text segment may be displayed by for example displaying each text segment in color corresponding to the emotional state of the user as explained above.

Figure 10:
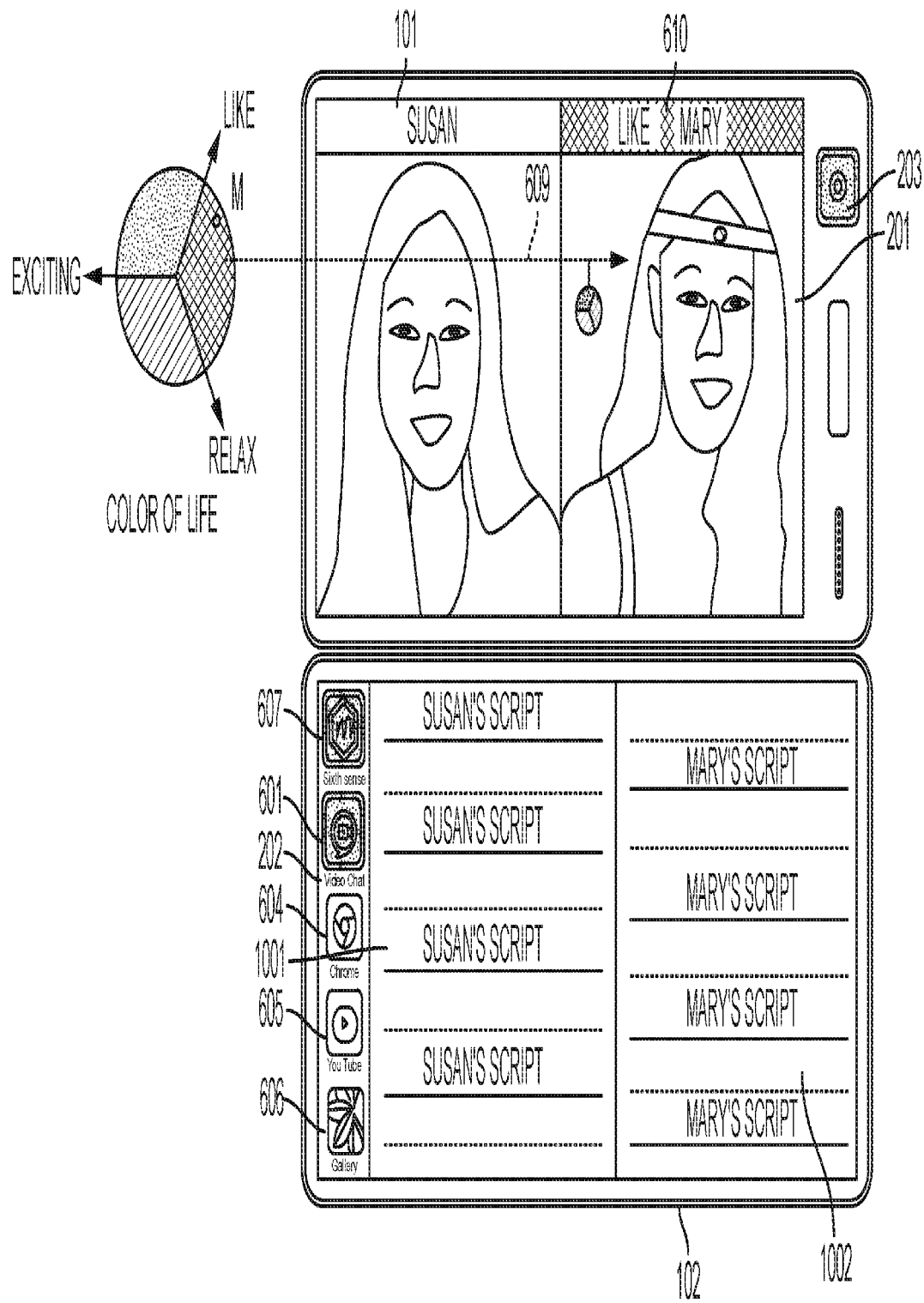
FIG. 10 is a view illustrating an apparatus providing, in real-time, one or more scripts or transcripts of a conversation and an emotional state of a user, while being in a communication mode, according to an exemplary embodiment.

FIG. 10 is a view illustrating an apparatus providing, in real-time, one or more scripts or transcripts of a conversation and an emotional state of a user, while being in a communication mode, according to an exemplary embodiment. As shown in FIG. 10, the second part 102 of the apparatus 100 has two screens 1001 and 1002. The first screen 1001 shows scripts of voice data uttered by the other entity, Susan and the second screen 1002 shows scripts of voice data uttered by the user Mary. According to an exemplary embodiment, each portion may be color-coded or provided in a distinct manner to show the cognitive or emotional state of the user of the apparatus.

As explained above, the generated data blocks of the communication while the apparatus is in the communication mode are recorded and stored in a memory. As a result, the user may review contents of the communication in a review mode, according to an exemplary embodiment.

Figure 11:
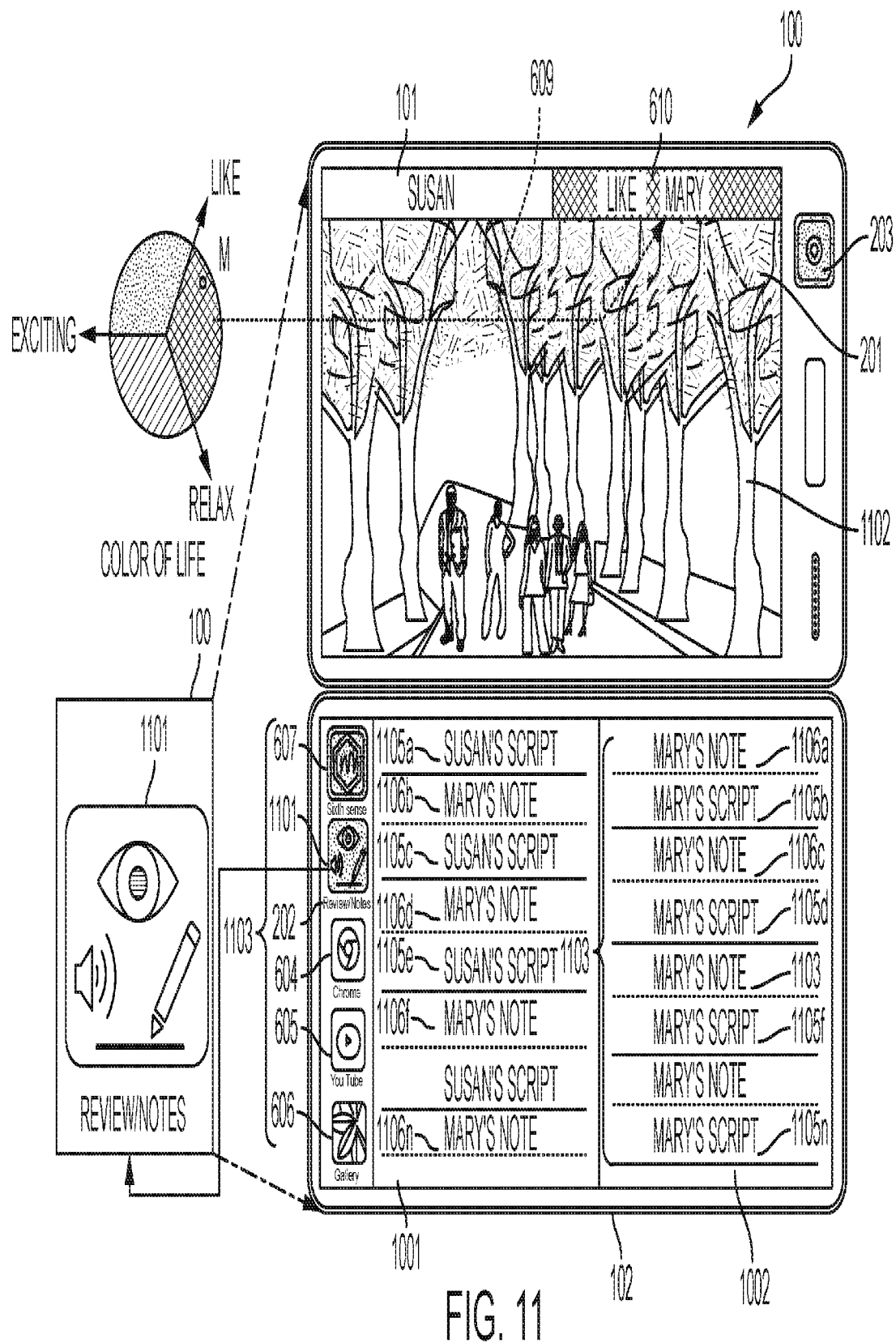
FIG. 11 is a view illustrating an apparatus providing secondary contents including review contents and an emotional state of the user, while being in a review mode, according to an exemplary embodiment.

FIG. 11 is a view illustrating an apparatus providing secondary contents including review contents and an emotional state of the user, while being in a review mode, according to an exemplary embodiment.

As shown in FIG. 11, once the apparatus completes the conversation mode, the user of the apparatus may select a review icon 1101, by way of an example. Since the communication mode is deactivated, the camera 203 is depicted in the deactivated state and the video chat icon 601 disappears from the display. Also, additional contents 1102 depicted during the conversation may be displayed on the first display 201. The second display 202 may display scripts of the recorded primary contents as Susan's scripts 1001 and Mary's scripts 1002 (explained above with reference to FIG. 10) and respective notes/comments can be made or the ones that were previously made 1103 by the user of the apparatus. That is, according to an exemplary embodiment, additional secondary contents 1103 may be displayed which is synchronized with each respective data block and may be notes made by the user. Additionally, the scripts 1001 and 1002 may be displayed in a manner which shows the cognitive or emotional state of the user of the device. The cognitive or emotional state may be the initial captured cognitive or emotional state of the user during the conversation or may be cognitive or emotional state of the user during the review stage (current state) or a combination of the two.

In an exemplary embodiment depicted above with reference to FIGS. 6 and 7, Mary is talking to her friend Susan. Her emotional state may be indicated by a color green because Mary likes the topic she is talking about. The color indicates her emotional state as being a mix of like (green). If it is yellowish, it may also indicate that she is excited about the topic. The screen may be depicted with a green color or a color coded icon may be provided on a screen indicating an emotional state of Mary. This is provided by way of an example and not by way of a limitation. Other techniques such are shading, or even a text or an icon indicating Mary's emotional state are within the scope of exemplary embodiments.

According to an exemplary embodiment, Mary's emotional state while the apparatus is in the conversation mode may be displayed with each script segment 1105*a*-1105*n* while Mary's emotional state may be displayed with each corresponding note segment 1106*a*-1106*n*. Accordingly, Mary may observe a change of her emotional state with respect to the primary contents during the conversation mode of the apparatus and during the review mode of the apparatus. For example, the user of the apparatus may no longer be excited by the memory and may now feel relaxed.

Figure 12A:
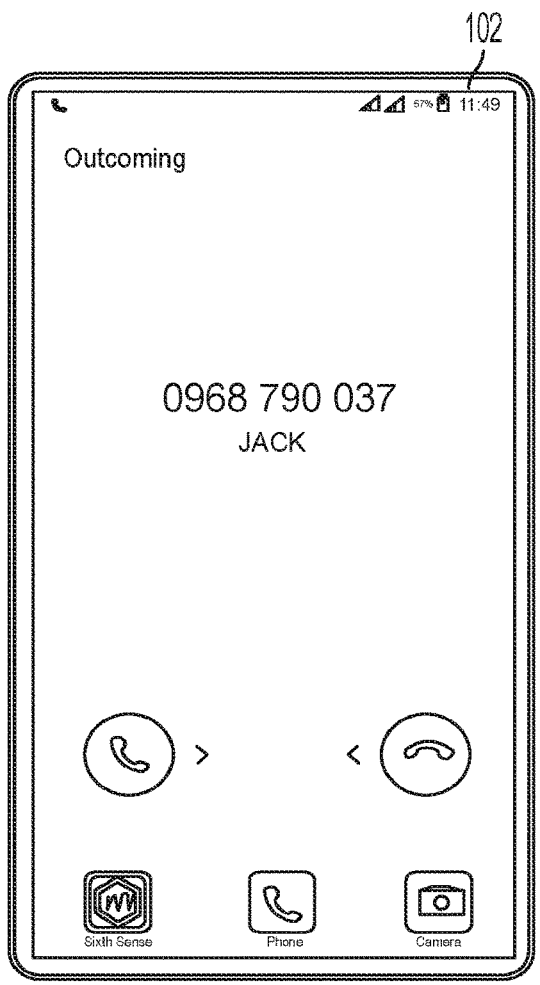
FIGS. 12A and 12B are views illustrating a front and a back, respectfully, of an apparatus in a fully open state entering a communication mode according to yet another exemplary embodiment.
Figure 12B:
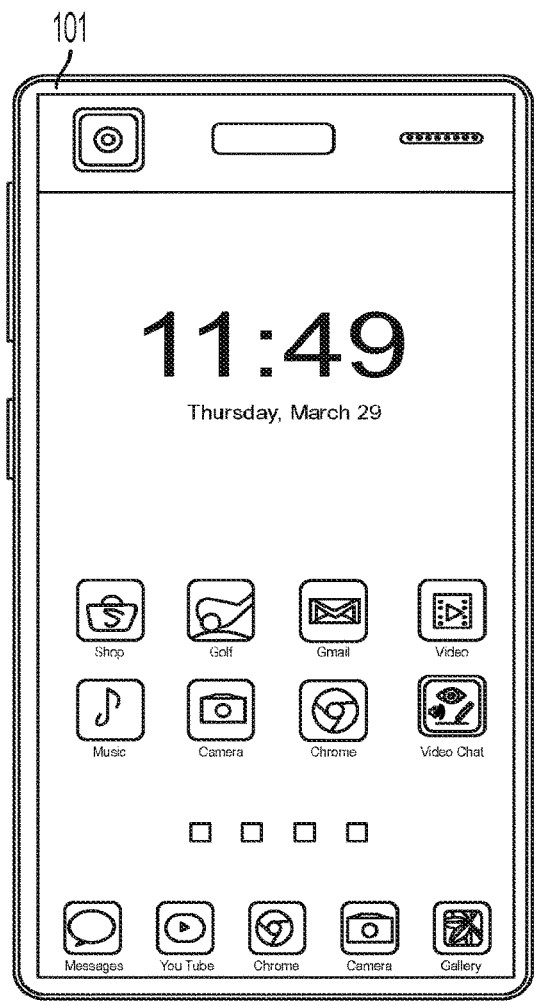

FIGS. 12A and 12B are views illustrating a front and a back, respectfully, of an apparatus in a fully open state entering a communication mode according to yet another exemplary embodiment. As shown in FIG. 12A, the front 102 of the apparatus 100 is displaying receiving a call from another entity such as the user's boyfriend, Jack, in real time according to an exemplary embodiment. FIG. 12B shows the back 101 of the apparatus 100 having a home screen with a plurality of icons for various functionalities of the apparatus 100 according to an exemplary embodiment.

Figure 13:
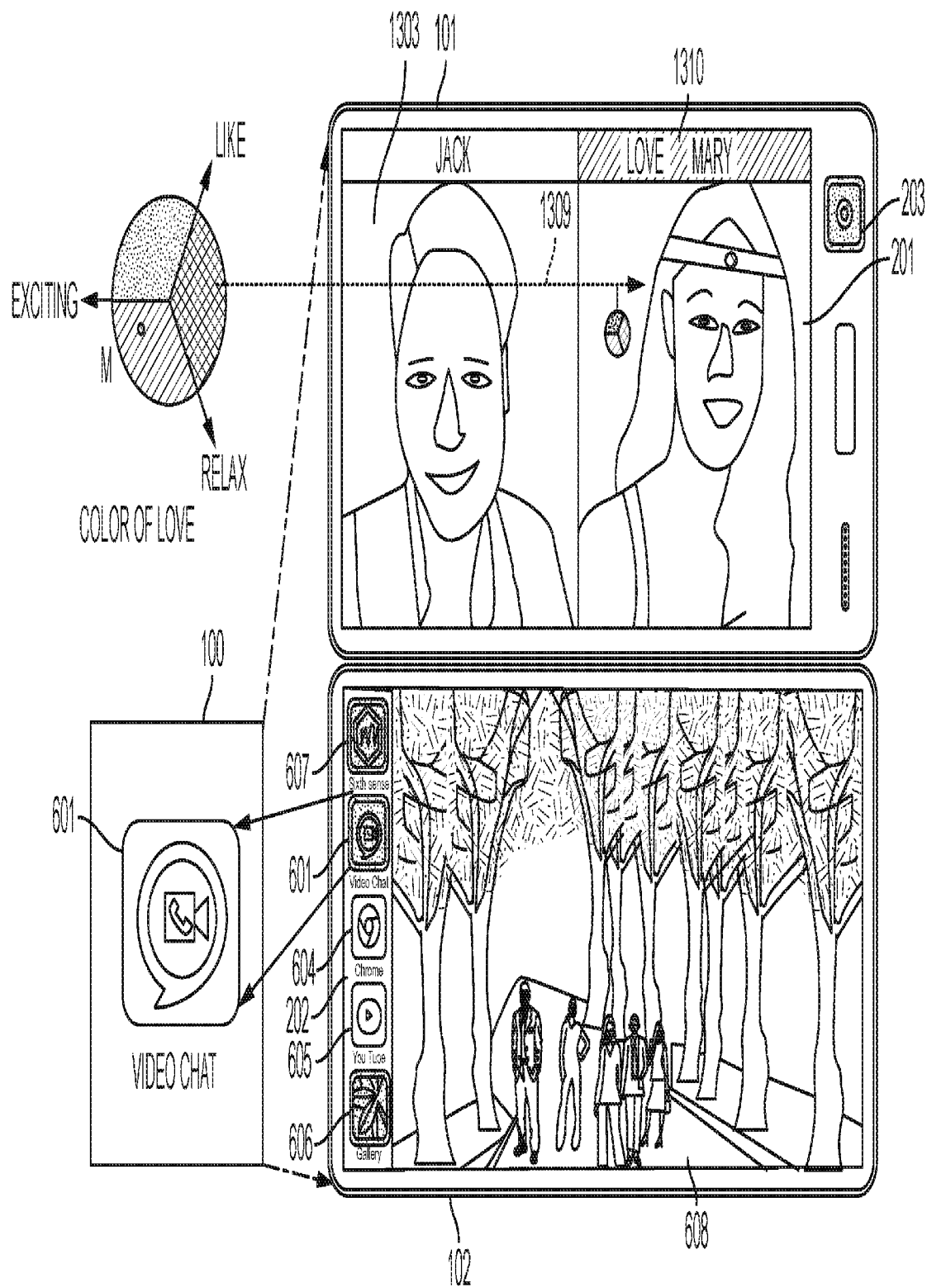
FIG. 13 is a view illustrating an apparatus providing an emotional state of a user while being in a communication mode, according to yet another exemplary embodiment.
Figure 14:
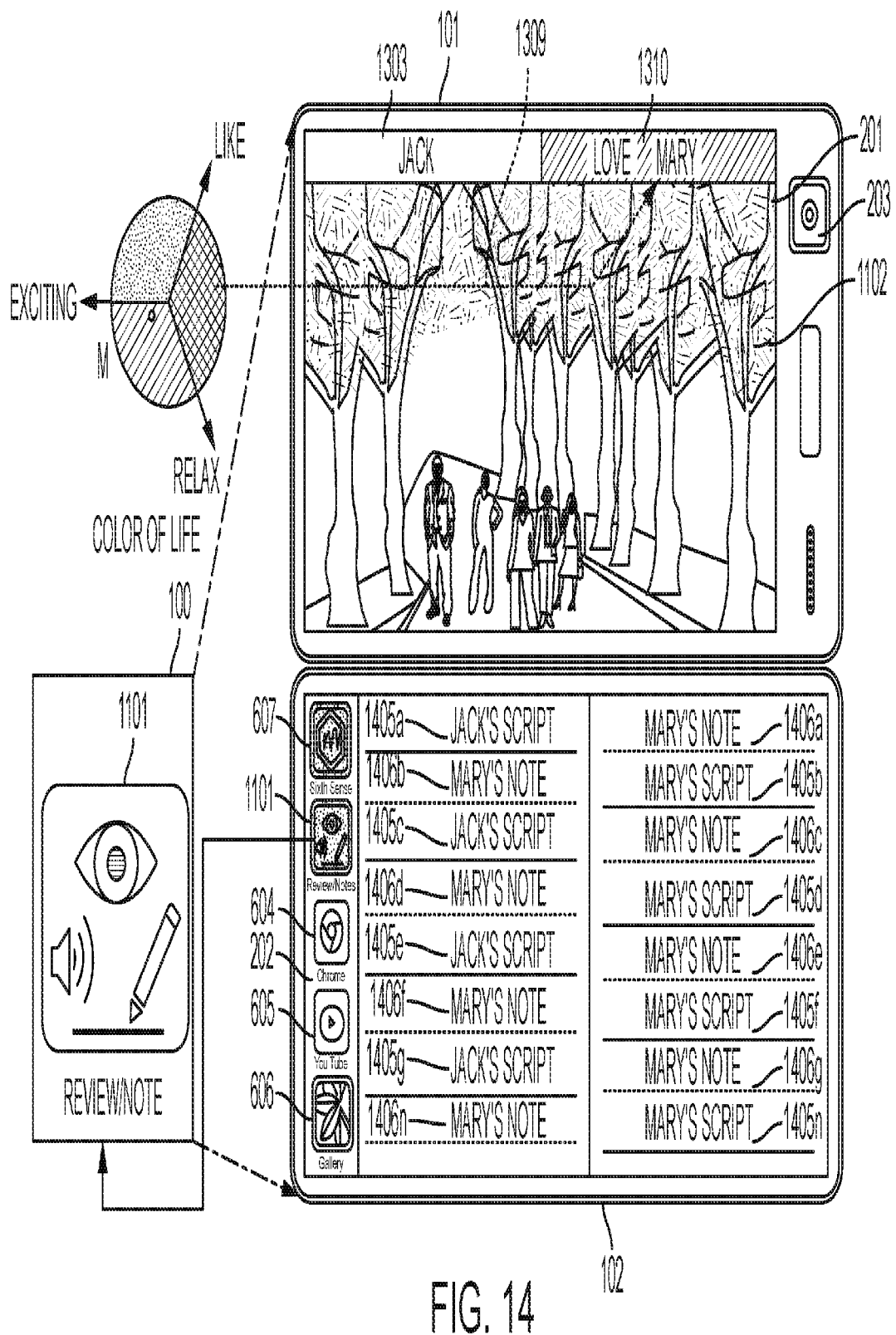
FIG. 14 is a view illustrating an apparatus providing secondary contents including review contents and an emotional state of the user, while being in a review mode, according to an exemplary embodiment.

According to an exemplary embodiment depicted in FIGS. 13 and 14, the apparatus is in a communication mode because the user has accepted the call with another entity, Jack.

FIG. 13 is a view illustrating an apparatus providing an emotional state of a user while being in a communication mode, according to yet another exemplary embodiment As shown in FIG. 13, Mary is now talking with her boyfriend 1303 (the other entity is now Jack). The color 1310 indicates her emotion is now red (love or excited). Jack can see how much Mary loves him when she is telling him a story or their memory together (if, of course, Mary allows him to see it). In an exemplary embodiment of FIG. 13, the screen may be shaded or color coded based on her emotional state or a separate icon or a text may be output on a display indicating Mary's emotional state. A color key 1309 may be provided as well.

In an exemplary embodiment, for all operations of the apparatus, the Fuvi icon 607 may be highlighted or emphasized indicating that the emotional state of the user is being monitored. In an exemplary embodiment, when the apparatus is not connected and/or does not receive emotional signals from the I SEE® headset, the icon 607 may be shown grayed it out i.e., depicted deactivated state of the device. In an exemplary embodiment, while the apparatus is operating, the emotional state of the user is being monitored and output onto one of the displays. Accordingly, the Fuvi icon 607 appears in an activated state.

FIG. 14 is a view illustrating an apparatus providing secondary contents including review contents and an emotional state of the user, while being in a review mode, according to yet another exemplary embodiment. In FIG. 14, the user's emotional state is determined to be love during the conversation mode as shown by the scripts 1405a-1405n and even during the review mode as shown by the notes 1406a-1406n.

Figure 15:
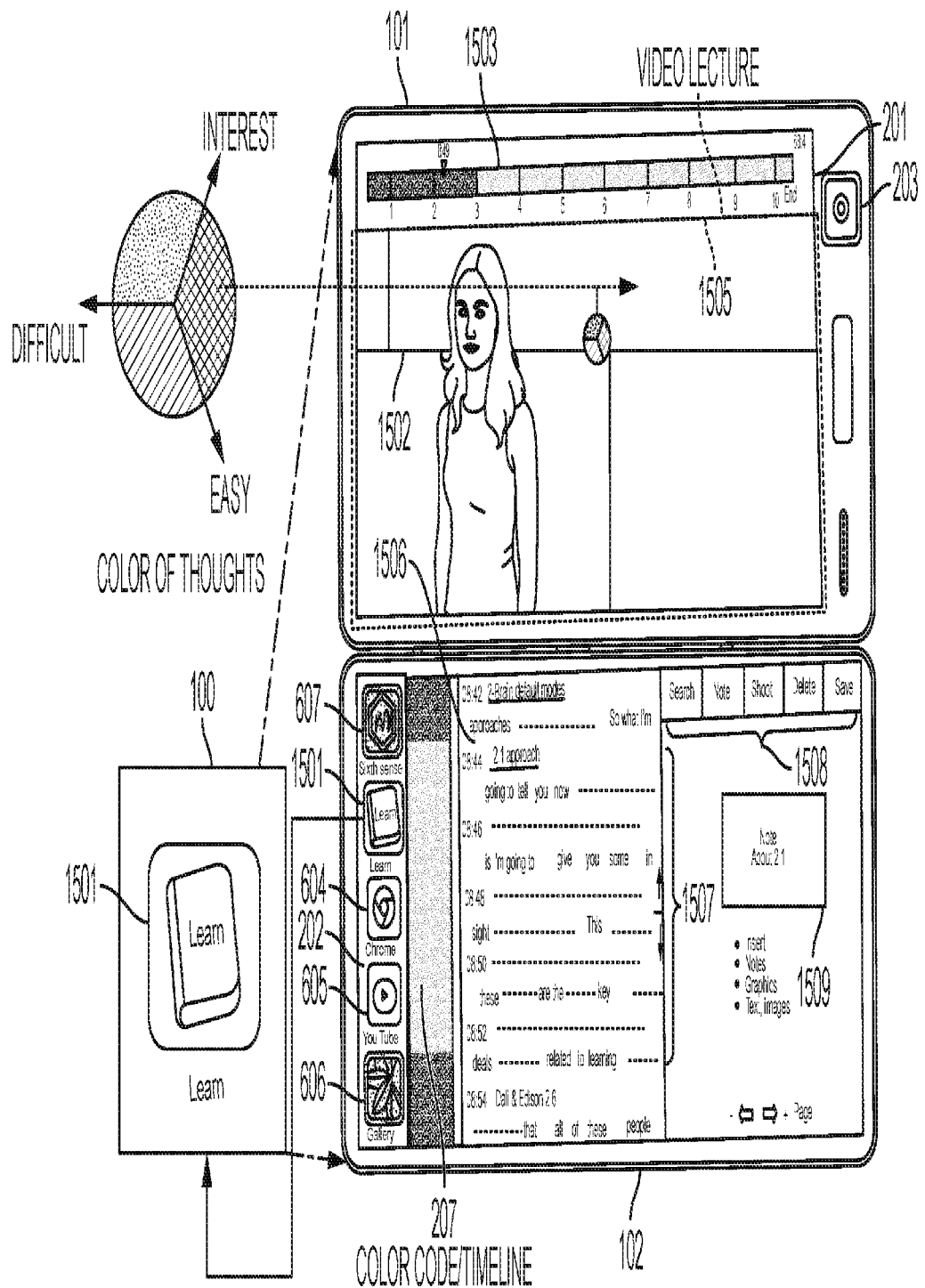
FIG. 15 is a view illustrating an apparatus providing primary contents, secondary contents, and an emotional state of the user while the apparatus is in a learning mode, according to yet another exemplary embodiment.

FIG. 15 is a view illustrating an apparatus providing primary contents, secondary contents, and emotional state while the apparatus is in a learning mode according to yet another exemplary embodiment.

As shown in FIG. 15, the apparatus enters the learning mode according to a user input of a selection of a learning icon 1501. When the learning icon 1501 is selected, the apparatus enters a learning mode in which the primary contents such as lecture 1502 is displayed on the first display 201 along with a corresponding timeline 1503. According to an exemplary embodiment, the primary contents are other than a conversation with another user and instead may be recording a lecture in a classroom or an environment of a user. FIG. 15 displays the primary contents as being an already recorded lecture but this is provided by way of an example and not by way of a limitation. The primary contents may be recorded in real time and color coded based on the emotional state of the user.

According to an exemplary embodiment depicted in FIG. 15, the FUVI icon is activated and the headset 500 is initiated or turned to an active state to record the environment and the emotional state of the user. As shown in FIG. 15, the key 1505 indicates color for each emotional state of the user. The lecture 1502 is being played to the user and the timeline may be color coded 1503 based on the emotional state of the user captured along with the lecture 1502. However, the secondary contents 1506 may include the text scripts 1507 which are color coded segments 1507a-1507n. The segments 1507a-1507n are color coded based on the currently captured user state. In other words, according to an exemplary embodiment shown in FIG. 15, the display 201 may provide the emotional state captured during the initial recording of the primary contents and the display 202 may provide emotional state in real time as the primary contents 1502 is being reviewed. In the review mode, the apparatus 100 includes additional functionality such as searching within the primary contents, adding notes, deleting portions, editing, and making changes and so on, as shown in menu options 1508. The secondary contents 1509 such as notes may be displayed on the second display 202 according to an exemplary embodiment. The descriptions of the various exemplary embodiments have been presented for purposes of illustration, but are not intended to be exhaustive or limited to the embodiments disclosed.

Many changes may be apparent to those of ordinary skill in the art without departing from the scope and spirit of the described embodiments. The terminology used herein was chosen to best explain the principles of the embodiments, the practical application or technical improvement over technologies found in the market place or to enable ordinary skill in the art to understand the embodiments disclosed herein.

In an exemplary embodiment, the term "computer-readable medium" as used herein refers to any medium that participates in providing instructions to a processor for execution. A computer readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable medium would include the following: an electrical connection having two or more wires, a portable computer diskette such as a floppy disk or a flexible disk, magnetic tape or any other magnetic medium, a hard disk., a random access memory (RAM), a read-only memory (ROM), an erasable programmable read-only memory (EPROM or Flash memory), a memory card, any other memory chip or cartridge, an optical fiber, a portable compact disc read-only memory (CD-ROM), any other optical medium, punchcards, papertape, any other physical medium with patterns of holes, or any other medium from which a computer can read or suitable combination of the foregoing.

In the context of this document, a computer readable medium may be any tangible, non-transitory medium that can contain, or store a program for use by or in connection with an instruction execution system, apparatus, or device.

Another form is signal medium and may include a propagated data signal with computer readable program code embodied therein, for example, in a base band or as part of a carrier wave. Such a propagated signal may take any of a variety of forms, including, but not limited to, the electro-magnetic, optical, or any suitable combination thereof. The signal medium may include coaxial cables, copper wire and fiber optics, including the wires that comprise data bus. The signal medium may be any medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc. or any suitable combination of the foregoing.

Computer program code for carrying out operations for aspects of the exemplary embodiments may be written in any combination of one or more programming languages, including an object oriented programming language such as Java, Smalltalk, C++, .Net or the like and conventional procedural programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an external computer (for example, through the Internet using an Internet Service Provider).

The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks. Volatile media includes dynamic memory.

Various forms of computer readable media may be involved in carrying one or more sequences of one or more instructions to a processor such as a CPU for execution. For example, the instructions may initially be carried on a magnetic disk from a remote computer. Alternatively, a remote computer can load the instructions into its dynamic memory and send the instructions over a telephone line using a modem. A modem local to a computer system can receive the data on the telephone line and use an infra-red transmitter to convert the data to an infra-red signal. An infra-red detector can receive the data carried in the infra-red signal and appropriate circuitry can place the data on the data bus. The bus carries the data to the volatile storage, from which processor retrieves and executes the instructions. The instructions received by the volatile memory may optionally be stored on persistent storage device either before or after execution by a processor. The instructions may also be downloaded into the computer platform via Internet using a variety of network data communication protocols well known in the art.

The flowchart and block diagrams in the Figures illustrate the architecture, functionality, and operation of possible implementations of systems, methods and computer program products according to various exemplary embodiments. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or two blocks may sometimes be executed in the reverse order, depending upon the functionality involved. It will also be noted that each block of the block diagram and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology as used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or acts for performing the function in combination with other claimed elements as specifically claimed.

The description of the exemplary embodiments has been presented for purposes of illustration and description, but is not intended to be exhaustive or limiting in any form. Many modifications and variations will be apparent to those of ordinary skill in the art without departing from the scope and spirit of the invention. Exemplary embodiments were chosen and described in order to explain operations and the practical applications thereof, and to enable others of ordinary skill in the art to understand various embodiments with various modifications as are suited to the particular use contemplated. That is, various modifications to these embodiments will be readily apparent to those skilled in the art, and the generic principles and specific examples defined herein may be applied to other embodiments without the use of inventive faculty. For example, some or all of the features of the different embodiments discussed above may be combined into a single embodiment. Conversely, some of the features of a single embodiment discussed above may be deleted from the embodiment. Therefore, the present disclosure is not intended to be limited to exemplary embodiments described herein but is to be accorded the widest scope as defined by the features of the claims and equivalents thereof.

What is claimed is:

1. A method of providing cognitive assistance comprising:
   establishing, by a first communication apparatus operated by a user, a communication with a second communication apparatus of a participant in the communication;
   receiving, by the first communication apparatus, first multimedia data generated by the second communication apparatus during the established communication;
   capturing, via an internal camera of the first communication apparatus, second multimedia data generated by the user during the established communication;
   displaying, on a first display of the first communication apparatus, content of the first multimedia data, the second multimedia data, or a third multimedia data generated during the established communication, the third multimedia data includes an environment of the user or the at least one participate or data downloaded via a network;
   displaying on a second display of the first communication apparatus, the first multimedia data including the participant and the second multimedia data including the user; and
   displaying cognitive state of the user on at least one from among the first display and the second display, wherein the cognitive state is obtained based on sensory data captured by a plurality of sensors on a headset worn by the user.

2. The method of claim 1, further comprising:
   receiving, by the first communication apparatus, the cognitive state of the user,
   wherein the cognitive state of the user is detected by a first remote apparatus and is processed by a second remote apparatus, and
   wherein the first communication apparatus is configured to communicate with the first remote apparatus via a wireless short range communication network and to communicate with the second remote apparatus via the network.

3. The method of claim 2, wherein the content of the communication is converted into a text format by the second remote apparatus and provided to the first communication apparatus and wherein the cognitive state of the user is converted into color codes by the second remote apparatus and is displayed on the second display of the first communication apparatus.

4. The method of claim 3, wherein displaying the content includes displaying, on the first display of the first communication apparatus, the content of the communication in the text format, highlighted with the color codes obtained based on the cognitive state of the user.

5. The method of claim 1, further comprising:
receiving, via a user interface of the first communication apparatus, user input related to whether to detect the cognitive state of the user.

6. The method of claim 5, wherein the user interface is a touch screen provided on at least one from among the first display and the second display.

7. The method of claim 1, wherein the cognitive state of the user is displayed on the second display with a cognitive state key map indicating codes for different cognitive states of the user and wherein the different cognitive states include excited state, liking state, and a relax state.

8. The method of claim 1, wherein the internal camera is configured to capture the user during the communication when the first communication apparatus is open at approximately 120 degrees and is configured to capture the environment of the user when the first communication apparatus is open more than 180 degrees.

9. A non-transitory computer readable medium configured to store instructions, which when executed by a processor cause the processor to execute the following operations:
connecting a first communication apparatus operated by a user to establish communication with a second communication apparatus of a participant;
obtaining, by the first communication apparatus, first multimedia data generated by the second communication apparatus during the communication;
capturing, via an internal camera of the first communication apparatus, second multimedia data generated by the user during the communication;
displaying, on a first display of the first communication apparatus, content of the first multimedia data, the second multimedia data, or a third multimedia data generated during the established communication, wherein the third multimedia data includes an environment of the user or the at least one participate or data downloaded via a network;
displaying on a second display of the first communication apparatus, the first multimedia data including the participant and the second multimedia data including the user; and
displaying cognitive state of the user on at least one from among the first display and the second display, wherein the cognitive state is obtained based on sensory data captured by a plurality of sensors on a headset worn by the user.

10. The non-transitory computer readable medium of claim 9, wherein the instructions further cause the processor to execute the following operation:
obtaining, by the first communication apparatus, the cognitive state of the user,
wherein the cognitive state of the user is detected by the headset and is processed by a remote apparatus, and
wherein the first communication apparatus is configured to communicate with the headset via a wireless short range communication network and to communicate with the remote apparatus via the network.

11. The non-transitory computer readable medium of claim 10, wherein the content of the communication is converted into a text format by the remote apparatus and provided to the first communication apparatus and wherein the cognitive state of the user is converted into color codes by the second remote apparatus and is displayed on the second display of the first communication apparatus.

* * * * *